(12) United States Patent
Boni et al.

(10) Patent No.: US 7,718,189 B2
(45) Date of Patent: *May 18, 2010

(54) SUSTAINED RELEASE OF ANTIINFECTIVES

(75) Inventors: Lawrence T. Boni, Monmouth Junction, NJ (US); Brian S. Miller, Mercerville, NJ (US); Vladimir Malinin, Plainsboro, NJ (US); Xingong Li, Robbinsville, NJ (US)

(73) Assignee: Transave, Inc., Monmouth Junction, NJ (US)

( * ) Notice: Subject to any disclaimer, the term of this patent is extended or adjusted under 35 U.S.C. 154(b) by 1218 days.

This patent is subject to a terminal disclaimer.

(21) Appl. No.: 11/185,448

(22) Filed: Jul. 19, 2005

(65) Prior Publication Data

US 2006/0073198 A1    Apr. 6, 2006

Related U.S. Application Data

(63) Continuation-in-part of application No. 11/023,971, filed on Dec. 28, 2004, now abandoned, which is a continuation-in-part of application No. 10/696,389, filed on Oct. 29, 2003, now Pat. No. 7,544,369.

(51) Int. Cl.
*A61K 9/127* (2006.01)
(52) U.S. Cl. .................................................. 424/450
(58) Field of Classification Search ................. 424/450
See application file for complete search history.

(56) References Cited

U.S. PATENT DOCUMENTS 4,372,949 A    2/1983   Kodama et al.
4,394,448 A    7/1983   Szoka, Jr. et al.
4,396,630 A    8/1983   Riedl et al.

(Continued)

FOREIGN PATENT DOCUMENTS

EP    0069307 A    1/1983

(Continued)

OTHER PUBLICATIONS

Alton et al., "Cationic lipid-mediated CFTR gene transfer to the lungs and nose of patients with cystic fibrosis: a double-blind placebo-controlled trial," The Lancet, 353:947-954 (1999).

(Continued)

*Primary Examiner*—Gollamudi S Kishore
(74) *Attorney, Agent, or Firm*—Foley Hoag, LLP

(57) ABSTRACT

Provided are lipid antiinfective formulations substantially free of anionic lipids with a lipid to antiinfective ratio is about 1:1 to about 4:1, and a mean average diameter of less than about 1 μm. Also provided is a method of preparing a lipid antiinfective formulation comprising an infusion process. Also provided are lipid antiinfective formulations wherein the lipid to drug ratio is about 1:1 or less, about 0.75:1 or less, or about 0.50:1 or less prepared by an in line fusion process. The present invention also relates to a method of treating a patient with a pulmonary infection comprising administering to the patient a therapeutically effective amount of a lipid antiinfective formulation of the present invention. The present invention also relates to a method of treating a patient for cystic fibrosis comprising administering to the patient a therapeutically effective amount of a lipid antiinfective formulation of the present invention.

79 Claims, 6 Drawing Sheets

U.S. PATENT DOCUMENTS

| | | | |
|---|---|---|---|
| 4,451,447 A | 5/1984 | Kaplan et al. | |
| 4,693,999 A | 9/1987 | Axelsson et al. | |
| 4,767,874 A | 8/1988 | Shima et al. | |
| 4,895,452 A | 1/1990 | Yiournas et al. | |
| 4,895,719 A | 1/1990 | Radhakrishnan et al. | |
| 4,897,384 A | 1/1990 | Janoff et al. | |
| 4,933,121 A | 6/1990 | Law et al. | |
| 4,952,405 A | 8/1990 | Yau-Young | |
| 4,975,282 A | 12/1990 | Cullis et al. | |
| 4,981,692 A * | 1/1991 | Popescu et al. | 424/422 |
| 5,000,958 A | 3/1991 | Fountain et al. | |
| 5,006,343 A | 4/1991 | Benson et al. | |
| 5,023,087 A | 6/1991 | Yau-Young | |
| 5,030,453 A | 7/1991 | Lenk et al. | |
| 5,049,388 A | 9/1991 | Knight | |
| 5,049,389 A | 9/1991 | Radhakrishnan | |
| 5,059,591 A | 10/1991 | Janoff et al. | |
| 5,077,056 A | 12/1991 | Bally et al. | |
| 5,169,637 A | 12/1992 | Lenk et al. | |
| 5,178,876 A | 1/1993 | Khokhar et al. | |
| 5,211,955 A | 5/1993 | Legros et al. | |
| 5,264,618 A | 11/1993 | Felgner et al. | |
| 5,269,979 A | 12/1993 | Fountain | |
| 5,279,833 A | 1/1994 | Rose | |
| 5,320,906 A | 6/1994 | Eley et al. | |
| 5,334,761 A | 8/1994 | Gebeyehu et al. | |
| 5,409,704 A | 4/1995 | Bally et al. | |
| 5,459,127 A | 10/1995 | Felgner et al. | |
| 5,540,936 A * | 7/1996 | Coe et al. | 424/450 |
| 5,543,152 A | 8/1996 | Webb et al. | |
| 5,569,464 A | 10/1996 | Endo et al. | |
| 5,616,334 A | 4/1997 | Janoff et al. | |
| 5,641,662 A | 6/1997 | Debs et al. | |
| 5,643,599 A | 7/1997 | Lee et al. | |
| 5,662,929 A * | 9/1997 | Lagace et al. | 424/450 |
| 5,665,383 A | 9/1997 | Grinstaff et al. | |
| 5,723,147 A | 3/1998 | Kim et al. | |
| 5,741,516 A | 4/1998 | Webb et al. | |
| 5,753,613 A | 5/1998 | Ansell et al. | |
| 5,756,120 A | 5/1998 | Hersch et al. | |
| 5,756,353 A | 5/1998 | Debs | |
| 5,759,571 A | 6/1998 | Hersch et al. | |
| 5,766,627 A | 6/1998 | Sankaram et al. | |
| 5,795,589 A | 8/1998 | Mayer et al. | |
| 5,820,848 A | 10/1998 | Boni et al. | |
| 5,843,473 A | 12/1998 | Woodle et al. | |
| 5,849,490 A | 12/1998 | Schonwetter et al. | |
| 5,875,776 A | 3/1999 | Vaghefi | |
| 5,945,122 A | 8/1999 | Abra et al. | |
| 6,045,828 A | 4/2000 | Bystrom et al. | |
| 6,051,251 A | 4/2000 | Zalipsky et al. | |
| 6,086,851 A * | 7/2000 | Boni et al. | 424/9.4 |
| 6,090,407 A | 7/2000 | Knight et al. | |
| 6,147,060 A | 11/2000 | Zasloff et al. | |
| 6,211,162 B1 | 4/2001 | Dale et al. | |
| 6,221,388 B1 * | 4/2001 | Hersch et al. | 424/450 |
| 6,352,996 B1 | 3/2002 | Cao et al. | |
| 6,419,901 B2 | 7/2002 | Placke et al. | |
| 6,440,393 B1 | 8/2002 | Waldrep et al. | |
| 6,451,784 B1 | 9/2002 | Placke et al. | |
| 6,497,901 B1 | 12/2002 | Royer | |
| 6,511,676 B1 | 1/2003 | Boulikas | |
| 6,599,912 B1 | 7/2003 | Au et al. | |
| 6,843,942 B2 | 1/2005 | Katinger et al. | |
| 7,544,369 B2 * | 6/2009 | Boni et al. | 424/450 |
| 2001/0006660 A1 * | 7/2001 | Lagace et al. | 424/400 |
| 2002/0086852 A1 | 7/2002 | Cantor et al. | |
| 2002/0187105 A1 | 12/2002 | Zou et al. | |
| 2003/0059375 A1 | 3/2003 | Perez-Soler et al. | |
| 2003/0118636 A1 | 6/2003 | Friesen et al. | |
| 2005/0019926 A1 * | 1/2005 | Gonda et al. | 435/455 |

FOREIGN PATENT DOCUMENTS

| | | |
|---|---|---|
| GB | 2145107 A | 3/1985 |
| WO | WO-86/06959 | 12/1986 |
| WO | WO-91/16882 | 11/1991 |
| WO | WO-93/12240 | 6/1993 |
| WO | WO-94/12155 | 6/1994 |
| WO | WO-94/12156 | 6/1994 |
| WO | WO-96/19199 | 6/1996 |
| WO | WO-96/19972 | 7/1996 |
| WO | WO-99/65466 | 12/1999 |
| WO | WO-00/27359 | 5/2000 |
| WO | WO-00/29103 | 5/2000 |
| WO | WO-03/075889 | 9/2003 |

OTHER PUBLICATIONS

Poyner et al., "A comparative study on the pulmonary delivery of tobramycin encapsulated into liposomes and PLA microspheres following intravenous and endotracheal delivery," Journal of Controlled Release, 35:41-48 (1995).

Schreier et al., "Pulmonary delivery of liposomes," Journal of Controlled Release, 24:209-233 (1993).

Sermet-Gaudelus et al., "Nebulized Antibiotics in Cystic Fibrosis," Paediatric Drugs, 4(7):455-467 (2002).

Supplementary European Search Report dated Jan. 12, 2009 for 03816990.0.

Antos et al., (1995) Antibacterial activity of liposomal amikacin against *Pseudomonas aeruginosa* in vitro. Pharmacological Research 32(1/2): 84-87.

Bakker-Woudenberg et al., (1995) Efficacy of gentamicin or ceftazidine entrapped in liposomes with prolonged blood circulation and enhanced localization in Klebsiella pneumoniae-infected lung tissue. Journal Infectious Diseases 171:938-947.

Bargoni et al., (2001) Transmucosl transport of tobramycin incorporated in solid lipid nanoparticles (SLN) after duodenal administration to rats. Part II—Tissue distribution. Pharmacological Research 43(5): 497-502.

Beaulac et al., (1997) In vitro kinetics of drug release and pulmonary retention of microencapsulated antibiotic in liposomal formulations in relation to the lipid composition. Journal Microencapsulation 14(3): 335-348.

Beaulac et al., (1999) Aerolization of low phase transition temperature liposomal tobramycin as a dry powder in an animal model of chronic pulmonary infection caused by *Pseudomonas aeruginosa*. Journal Drug Targeting 7(1): 33-41.

Bermudez et al., (1999) Treatment of Disseminated Mycobacterium avium Complex Infection of Beige Mice with Liposome-Encapsulated Aminoglycosides. Journal Infect. Dis. 161: 1262-1268.

Bucke et al., (1997) Surface-Modified Amikacin-Liposomes: Organ Distribution and Interaction with Plasma Proteins. Journal Drug Targeting 5(2): 99-108.

Comis, "Carboplatin in the Treatment of Non-Small Cell Lung Cancer: a Review," *Oncology*, Nov. 1993; 50 (2): 37-41. (Abstract).

Cynamon et al., (1989) Liposome-Encapsulated-Amikacin Therapy of Mycobacterium avium Complex Infection in Geige Mice. Antimicrobial Agents and Chemotherapy 33(8): 1179-1183.

Dees et al., (1990) The mechanism of enhanced intraphagocytic killing of bacteria by liposomes containing antibiotics. Veterinary Immunology and Immunopathology 24: 135-146.

Demaeyer et al., (1993) Disposition of liposomal gentamicin following intrabronchial administration in rabbits. Journal Microencapsulation 10(1): 77-88.

Ehlers et al., (1996) Liposomal amikacin for treatment of M. avium Infections in clinically relevant experimental settings. Zbl. Bakt. 284: 218-231.

Fielding et al., (1999) Pharmacokinetics and Urinary Excretion of Amikacin in Low-Clearance Unilamellar Liposomes after a Single or Repeated Intravenous Administration in the Rhesus Monkey. Antimicrobial Agents and Chemotherapy 43(3): 503-509.

Fountain et al., (1985) Treatment of Brucella canis and Brucella abortus in vitro and in vivo by stable plurilamellar vesicle-encapsulated aminoglycosides. Journal Infectious Diseases 152(3): 529-535.

Howell, S.B., (2001) Clinical applications of a novel sustained-release injectable drug delivery system: Depofoam Technology. Cancer Journal 7: 219-227.

Katare, O.P., et al., Enhanced in vivo Performance of Liposomal Indomethacin Derived From Effervescent Granule Based Proliposomes, J. Microencapsulation, 1995, vol. 12, No. 5, pp. 487-493.

Kesavalu et al., (1990) Differential effects of free and liposome encapsulated amikacin on the survival of Mycobacterium avium complex in mouse peritoneal macrophages. Tubercle 71: 215-218.

Kim et al., (1990) Pharmacokinetics of intravitreally injected liposomes encapsulated tobramycin in normal rabbits. Yonsei Medical Journal 31(4): 308-314.

Klemens et al., (1990) Liposome-encapsulated-gentamicin therapy of Mycobacterium avium complex infection in beige mice. Antimicrobial Agents and Chemotherapy 34(6) 967-970.

Lagace et al., (1991) Liposome-encapsulated antibiotics: preparation, drug release and antimicrobial activity against *Pseudomona aeruginosa*. Journal Microencapsulation 8(1): 53-61.

Lutwyche et al., (1998) Intracellular delivery and antibacterial activity of gentamicin encapsulated in pH-sensitive liposomes. Antimicrobial Agents and Chemotherapy 42(10) 2511-2520.

Marier et al., (2003) Liposomal tobramycin against pulmonary infections of *Pseudomonas aeruginosa*: a pharmacokinetic and efficacy study following single and multiple intratracheal administrations in rats. Journal Antimicrobial Chemotherapy 52: 247-252.

Morgan et al., (1980) Preparation and properties of liposome-associated gentamicin. Antimicrobial Agents and Chemotherapy 17(4) 544-548.

Nightingale et al., (1993) Liposome-encapsulated gentamicin treatment of Mycobacterium avium-Mycobacterium intracellulare complex bacteremia in AIDS patients. Antimicrobial Agents and Chemotherapy 37(9) 1869-1872.

Niven, Ralph et al., Nebulization of Liposomes. I. Effects of Lipid Composition, Report, pp. 1127-1133.

Omri et al., (1994) Pulmonary retention of free and liposome-encapsulated tobramycin after intratracheal administration in uninfected rats and rats infected with *Pseudomonas aeruginosa*. Antimicrobial Agents and Chemotherapy 38(5) 1090-1095.

Omri et al., (1995) Incorporation, release and in vitro antibacterial activity of liposomal aminoglycosides against *Pseudomonas aeruginosa*. Journal Antimicrobial Chemotherapy 36: 631-639.

Omri et al., (1996) Comparison of the Bactericidal Action of Amikacin, Netilmicin and Tobramtcin in Free and Liposomal Formulation against *Pseudomonas aeruginosa*. Chemotherapy 42: 170-176.

Petersen et al., (1996) Liposomal amikacin: improved treatment of Mycibacterium avium complex infection in the beige mouse model. Journal Antimicrobial Chemotherapy 38: 819-828.

Petkowicz, Jozefa, et al., Hypoglycemic Effect of Liposome-Entrapped Insulin Administered by Various Routes into Normal Rats, Pol. J. Pharmacol. Pharm., 1989, 41, pp. 299-304.

Poyner et al., (1993) Preparation, properties and the effects of free and liposomal tobramycin on siderophore production by *Pseudomonas aeruginosa*. Journal Antimicrobial Chemotherapy 34: 43-52.

Price et al., (1989) Enhanced effectiveness of intraperitoneal antibiotics administered via liposomal carrier. Arch Surgery 124: 1411-1415.

Price et al., (1992) Liposome delivery of aminoglycosides in burn wounds. Surgery, Gynecology &Obstetrics 174: 414-418.

Price et al., (1994) Liposome encapsulation: a method for enhancing the effectiveness of local antibiotics. Surgery, 115(4): 480-4487.

Ramsammy et al., (1988) The effect of gentamicin on the biophysical properties of phosphatidic acid liposomes is influenced by the O-C=O group of the lipid. Biochemistry 27: 8249-8254.

Roehrborn et al., (1995) Lipid-based slow-release formulation of amikacin sulfate reduces foreign body associated infections in mice. Antimicrobial Agents Chemotherapy 39: 1752-1755.

Schiffelers et al., (2001) In vivo synergistic interaction of liposome-coencapsulated gentamicin and ceftazidime. Journal Pharmacology Experimental Therapeutics 298(1): 369-375.

Schiffelers et al., (2001) Therapeutic efficacy of liposomal gentamicin in clinically relevant rat models. International Journal Pharmaceutics 214: 103-105.

Swenson et al., (1990) Pharmacokinetics and in vivo activity of liposome-encapsulated gentamicin. Antimicrobial Agents and Chemotherapy 34(2) 235-240.

Trafny et al., (1995) Effects of free and liposome-encapsulated antibiotics on adherence of *Pseudomonas aeruginosa* to collagen type I. Antimicrobial Agents and Chemotherapy 39(12) 2645-2649.

Vitas et al., (1996) Effect of composition and method of preparation of liposomes on their stability and interaction with murine monocytes infected with Brucella abortus. Antimicrobial Agents and Chemotherapy 40(1) 146-151.

Whitehead et al., (1998) Kinetics and Toxicity of Liposomal and conventional Amikacin in a Patient with a Multidrug-Resistant Tuberculosis. Eur J Clin Microbiol Infect Dis 17: 794-797.

Yanagihara, K. (2002) Design of anti-bacterial drug and anti-Mycobacterial drug for drug delivery system. Current Pharmaceutical Design 8: 475-482.

Zeng et al., (1993) Intravitreal Pharmacokinetics of Liposome-encapsulated Amikacin in a Rabbit Model. Opthamology 100: 1640-1644.

Zhang et al., (1999) A Novel Method to Prepare Liposomes Containing Amikacin. Journal Microencapsulation 16(4): 511-516.

Beaulac et al., "Eradication of Mucoid *Pseudomonas aeruginosa* with Fluid Liposome-Encapsulated Tobramycin in an Animal Model of Chronic Pulmonary Infection," Antimicrobial Agents and Chemotherapy, 40(3):665-669 (1996).

Beaulac et al., "In-vitro bactericidal efficacy of sub-MIC concentrations of liposome-encapsulated antibiotic against Gram-negative and Gram-positive bacteria," Journal of Antimicrobial Chemotherapy, 41:35-41 (1998).

Deol et al., "Lung specific stealth liposomes: stability, biodistribution and toxicity of liposomal antitubular drugs in mice," Biochemica et Biophysica Acta, 1334:161-172 (1997).

Xiu et al., "Drug Resistant Analysis of *Pseudomonas Aeruginosa* in Patients with Mechanical Ventilation," Med. J. Chin. PLA, 27(6):544-545 (2002).

\* cited by examiner

SUSTAINED RELEASE OF ANTIINFECTIVES

RELATED APPLICATIONS

This application is a continuation-in-part of U.S. patent application Ser. No. 11/023,971, filed Dec. 28, 2004, which is a continuation-in-part of U.S. patent application Ser. No. 10/696,389, filed Oct. 29, 2003, which claims the benefit of U.S. Provisional Patent Application Ser. No. 60/421,923, filed Oct. 29, 2002.

INTRODUCTION

Certain sustained release technology suitable for administration by inhalation employs liposomes and lipid complexes to provide prolonged therapeutic effect of drug in the lung and systemically by sustained release and the ability to target and enhance the uptake of drug into sites of disease. The present invention comprises a liposomal antiinfective, and methods for treatment of pulmonary infections using liposomal or lipid-complexed antiinfective.

As reported in *Goodman and Gilman's The Pharmaceutical Basis of Therapeutics*, Eighth Edition, "Since the incidence of nephrotoxicity and ototoxicity is related to the concentration to which an aminoglycoside accumulates, it is critical to reduce the maintenance dosage of these drugs in patients with impaired renal function." Since aminoglycosides can produce vestibular or auditory dysfunction and nephrotoxicity regardless of a patient's impairments, it is important generally to reduce maintenance dosages. The present invention provides dramatic reductions in toxicity thus allowing higher doses than usual.

Cystic fibrosis (CF) patients have thick mucous and/or sputum secretions in the lungs, frequent consequential infections, and biofilms resulting from bacterial colonizations. All these fluids and materials create barriers to effectively targeting infections with antiinfectives. The present invention overcomes these barriers, and even allows reduced dosing (in amount or frequency), thereby reducing the drug load on patients. For lung infections generally, the dosing schedule provided by the invention provides a means of reducing drug load.

For a liposomal drug delivery system, it is often desirable to lower the lipid-to-drug (L/D) ratio as much as possible to minimize the lipid load to avoid saturation effects in the body. For lung delivery by inhalation, this may be particularly true because for chronic use, dosing of liposomes could outpace clearance thus limiting the administration and thus effectiveness of the drug product. A lower L/D ratio would allow more drug to be given before the dosing/clearance threshold is met.

SUMMARY OF INVENTION

Via infusion methods disclosed herein, liposomes substantially free of anionic lipids of modest size (<1 µm) that entrap antiinfectives at a lipid/antiinfective weight ratio of typically about 4:1 to about 0.5:1 have been created. The captured volumes of liposomes have been measured, and from these numbers one is able to calculate what the theoretical entrapment should be if the antiinfective behaved as an ideal solute (i.e., does not interact with the liposome membrane but entraps ideally along with water). From this comparison, entrapment numbers that are 3-5× higher than expected are observed, indicating that a special interaction is occurring that allows greater than expected entrapment, and lower than expected lipid/antiinfective ratios. The solution in which the liposomes form contains a concentration of antiinfective, the concentration of antiinfective inside the liposomes should be about the same concentration as in the solution. However, the internal antiinfective concentration is calculated to be at least about 3× higher.

In part, the present invention features a liposomal anitiinfective formulation comprising a lipid formulation and an antiinfective, wherein the lipid formulation is substantially free of anionic lipids, and wherein the weight ratio of lipid to antiinfective is about 4:1 to about 1:1. In certain embodiments, the weight ratio of lipid to antiinfective is about 3:1 to about 1:1, 2:1 to about 1:1, or about 1:1.

In another embodiment, the present invention relates to a lipid formulation comprising an antiinfective wherein the lipid to antiinfective ratio is about 1:1 or less, about 0.75:1 or less, or about 0.5:1 or less.

In certain embodiments, the lipid antiinfective formulation comprises a liposome having a mean diameter of about 0.2 µm to about 1.0 µm. In certain other embodiments, the mean diameter is about 0.2 µm to about 0.5 µm. In certain other embodiments, the mean diameter is about 0.2 µm to about 0.3 µm.

In certain embodiments, the antiinfective can be any antiinfective commonly known in the art. In certain emobodiments, the antiinfective can be an aminoglycoside including, but not limited to, amikacin, tobramycin, or gentamicin, or a pharmaceutically acceptable salt thereof.

In certain embodiments, the lipid formulation comprises a neutral lipid. In certain embodiments, the lipid formulation is free of anionic lipids. In certain other embodiments, the lipid is a phospholipid, including but not limited to, a phosphatidyl choline such as dipalmitoylphosphatidyl choline or dioleoylphosphatidyl choline; or the lipid can be a steroid such as a sterol, including, but not limited to, cholesterol; or the lipid can be a combination thereof.

In part, the present invention features a method of preparing the lipid antiinfective formulation described above comprising infusing an aqueous or alcoholic solution or mixture of the antiinfective with a lipid-alcohol solution or mixture at a temperature below the phase transition of at least one of the lipid components of the neutral lipid, wherein infusing is done from above. In certain embodiments, the alcohol is ethanol.

In certain embodiments, the concentration of the lipid-alcohol solution or mixture is about 10 to about 30 mg/mL. In certain embodiments, the concentration of the antiinfective aqueous or alcoholic solution or mixture is about 20 to about 70 mg/mL. In certain embodiments, the concentration of the neutral lipid-alcohol solution or mixture is about 10 to about 30 mg/mL, and the concentration of the antiinfective aqueous or alcoholic solution or mixture is about 20 to about 70 mg/mL. However, one of ordinary skill in the art will appreciate that concentrations may vary or otherwise be optimized depending on the lipid and/or antiinfective involved.

In certain embodiments, the present invention relates to the aforementioned lipid formulation, wherein the antiinfective is selected from the following: an aminoglycoside, a tetracycline, a sulfonamide, p-aminobenzoic acid, a diaminopyrimidine, a quinolone, a β-lactam, a β-lactam and a β-lactamase inhibitor, chloraphenicol, a macrolide, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, terbinafine, or combination thereof. In certain embodiments, the present invention relates to the aforementioned lipid formulation, wherein the antiinfective is an aminoglycoside. In a further embodiment, the antiinfective is an aminoglycoside selected from the following: amikacin, gentamicin, or tobramycin. In a further embodiment, the antiinfective is amikacin. In a further embodiment, the antiinfective is gentamicin. In a further embodiment, the antiinfective is tobramycin.

In certain embodiments, the present invention relates to the aforementioned lipid formulation, wherein the lipid formulation is a liposome.

In certain embodiments, the present invention relates to the aforementioned lipid formulation, wherein the lipid formulation comprises a phospholipid. In certain embodiments, the lipid formulation comprises a steroid. In certain embodiments, the lipid formulation comprises a sterol. In certain embodiments, the lipid formulation comprises dipalmitoylphosphatidylcholine (DPPC). In certain embodiments, the lipid formulation comprises cholesterol. In certain embodiments, the lipid formulation comprises a phospholipid and a steroid. In certain embodiments, the lipid formulation comprises a phospholipid and a sterol. In certain embodiments, the lipid formulation comprises DPPC and cholesterol. In certain embodiments, the present invention relates to the aforementioned formulation, wherein the lipid formulation comprises DPPC, dioleoylphosphatidylcholine (DOPC), and cholesterol.

In certain embodiments, the present invention relates to the aforementioned formulation, wherein the lipid formulation comprises DPPC and cholesterol in a mole ratio of about 20:1, 10:1, 5:1, 2:1, or 1:1.

In certain embodiments, the present invention relates to the aforementioned formulation, wherein the lipid formulation comprises DPPC, DOPC, and cholesterol in a mole ratio of about 5-20:1-20:0.5-1.

In certain embodiments, the present invention relates to the aforementioned lipid formulation, wherein the lipid formulation is a liposome and the antiinfective is amikacin.

In certain embodiments, the present invention relates to the aforementioned lipid formulation, wherein the lipid formulation is a liposome, the antiinfective is amikacin, and the lipid formulation comprises a phospholipid and a sterol.

In certain embodiments, the present invention relates to the aforementioned lipid formulation, wherein the lipid formulation is a liposome, the antiinfective is amikacin, and the lipid formulation comprises a DPPC and a cholesterol.

In another embodiment, the present invention relates a method of preparing a lipid formulation comprising an antiinfective comprising: mixing a stream of a lipid solution or mixture, with a stream of an antiinfective solution or mixture, wherein the two streams are mixed in line. In certain embodiments, the two streams enter a Y-connector prior to mixing in line.

In certain embodiments, the present invention relates to the aforementioned method, wherein the stream of a lipid solution or mixture, and the stream of an antiinfective solution or mixture are mixed at a total flow rate of about 700 to about 900 mL/min. In certain embodiments, the stream of a lipid solution or mixture, and the stream of an antiinfective solution or mixture are mixed at a total flow rate of about 800 mL/min. In certain embodiments, the stream of a lipid solution or mixture is added at a flow rate of about 200 to about 400 mL/min. In certain embodiments, the stream of a lipid solution or mixture is added at a flow rate of about 300 mL/min. In certain embodiments, the stream of an antiinfective solution or mixture is added at a flow rate of about 400 to about 600 mL/min. In certain embodiments, the stream of an antiinfective solution or mixture is added at a flow rate of about 500 mL/min. In certain embodiments, the stream of a lipid solution or mixture is added at a flow rate of about 300 mL/min, and the stream of an antiinfective solution or mixture is added at a flow rate of about 500 mL/min.

In certain embodiments, the present invention relates to the aforementioned method, wherein the temperature of the combined streams is about 30-40° C. In certain embodiments, the temperature of the lipid solution or mixture is about 30° C., and the temperature of the antiinfective solution or mixture is about 30° C. In certain embodiments, the temperature of the lipid solution or mixture is about 50° C., and the temperature of the antiinfective solution or mixture is room temperature.

In certain embodiments, the present invention relates to the aforementioned method, wherein the method of preparing a lipid formulation comprising an antinfective further comprises the step of diluting the combined streams with water at least about 20 seconds after mixing.

In certain embodiments, the present invention relates to the aforementioned method, wherein the concentration of the antiinfective solution or mixture is about 30 to about 50 mg/mL. In certain embodiments, the concentration of the antiinfective solution or mixture is about 40 to about 50 mg/mL.

In certain embodiments, the present invention relates to the aforementioned method, wherein the stream of a lipid solution or mixture is added at a flow rate of about 300 mL/min, and the stream of an antiinfective solution or mixture is added at a flow rate of about 500 mL/min; the temperature of the combined streams is about 30-40° C.; the combined streams are diluted with water at least about 20 seconds after mixing; and the concentration of the antiinfective solution or mixture is about 40 to about 50 mg/mL.

In certain embodiments, the present invention relates to the aforementioned method, wherein the solutions or mixtures are aqueous or alcoholic. In certain embodiments, the present invention relates to the aforementioned method, wherein the lipid formulation is a liposome.

In certain embodiments, the present invention relates to the aforementioned method, wherein the antiinfective is selected from the following: an aminoglycoside, a tetracycline, a sulfonamide, p-aminobenzoic acid, a diaminopyrimidine, a quinolone, a β-lactam, a β-lactam and a β-lactamase inhibitor, chloraphenicol, a macrolide, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, terbinafine, or combination thereof. In certain embodiments, the antiinfective is an aminoglycoside. In certain embodiments, the antiinfective is an aminoglycoside selected from the following: amikacin, gentamicin, or tobramycin. In certain embodiments, the antiinfective is amikacin. In certain embodiments, the antiinfective is gentamicin. In certain embodiments, the antiinfective is tobramycin.

In certain embodiments, the present invention relates to the aforementioned method, wherein the lipid comprises a phospholipid. In certain embodiments, the lipid comprises a steroid. In certain embodiments, the lipid comprises a sterol. In certain embodiments, the lipid comprises DPPC. In certain embodiments, the lipid comprises cholesterol. In certain embodiments the lipid comprises a phospholipid and a sterol. In certain embodiments, the lipid comprises DPPC and cholesterol.

In certain embodiments, the present invention relates to the aforementioned method, wherein the lipid formulation is a liposome and the antiinfective is amikacin.

In certain embodiments, the present invention relates to the aforementioned method, wherein the lipid formulation is a liposome, the antiinfective is amikacin, and the lipid comprises a phospholipid and a sterol.

In certain embodiments, the present invention relates to the aforementioned method, wherein the lipid formulation is a liposome, the antiinfective is amikacin, and the lipid comprises DPPC and cholesterol.

In certain embodiments, the present invention relates to the aforementioned method, wherein the lipid formulation has a lipid to antiinfective ratio of about 1:1 or less.

In certain embodiments, the present invention relates to the aforementioned method, wherein the lipid formulation has a lipid to antiinfective ratio of about 0.75:1 or less.

In certain embodiments, the present invention relates to the aforementioned method, wherein the lipid formulation has a lipid to antiinfective ratio of about 0.5:1 or less.

In certain embodiments, the present invention relates to the aforementioned method, wherein the lipid formulation is a liposome, the antiinfective is amikacin, the lipid comprises DPPC and cholesterol, and the lipid to antiinfective ratio is about 1:1 or less.

In another embodiment, the present invention relates to a method of treating pulmonary infections in a patient in need thereof comprising administering to the patient a therapeutically effective amount of a liposomal antiinfective formulation comprising a lipid formulation and an antiinfective, wherein the dosage of antiinfective is about 100 mg/day or less. In a further embodiment, the dosage amount of antiinfective is about 30 mg to about 50 mg every other day. In a further embodiment, the dosage amount of antiinfective is about 30 mg to about 50 mg every third day.

In another embodiment, the present invention relates to the aforementioned method of treating, wherein the liposome has a mean diameter of about 0.2 μm to about 1.0 μm. In a further embodiment, the liposome has a mean diameter of about 0.2 μm to about 0.5 μm, or about 0.2 μm to about 0.3 μm.

In another embodiment, the present invention relates to the aforementioned method of treating, wherein the pulmonary infection is a result of cystic fibrosis.

In another embodiment, the present invention relates to the aforementioned method of treating, wherein the weight ratio of lipid to antiinfective is about 4:1 to about 0.5:1, about 3:1 to about 0.5:1, about 2:1 to about 0.5:1, or about 1:1 to about 0.5:1.

In another embodiment, the present invention relates to the aforementioned method of treating, wherein the antiinfective is selected from the following: an aminoglycoside, a tetracycline, a sulfonamide, p-aminobenzoic acid, a diaminopyrimidine, a quinolone, a β-lactam, a β-lactam and a β-lactamase inhibitor, chloraphenicol, penicillins, cephalosporins, a macrolide, linomycin, clindamycin, coricosteroids, prostaglandin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, terbinafine, or combination thereof. In another embodiment, the antiinfective is an aminoglycoside. In another embodiment, the antiinfective is amikacin.

In another embodiment, the present invention relates to the aforementioned method of treating, wherein the lipid formulation comprises neutral lipids. In another embodiment, the lipids that make up the lipid formulation are all neutral lipids. In another embodiment, the liposome is free of anionic lipids. In another embodiment, the lipid formulation comprises a phospholipid. In another embodiment, the lipid formulation comprises a sterol. In another embodiment, the lipid formulation comprises DPPC and cholesterol.

In another embodiment, the present invention relates to the aforementioned method of treating, wherein the antiinfective is amikacin, and the lipid formulation comprises DPPC and cholesterol.

In another embodiment, the present invention relates to the aforementioned method of treating, wherein the antiinfective is amikacin, the weight ratio of lipid to antiinfective is about 4:1 to about 1:1, and the lipid formulation comprises DPPC and cholesterol. In a further embodiment, the weight ratio is about 3:1 to about 1:1, 2:1 to about 1:1, or about 1:1.

In another embodiment, the present invention relates to the aforementioned method of treating, wherein the antiinfective is amikacin, the weight ratio of lipid to antiinfective is about 4:1 to about 1:1, the lipid formulation comprises DPPC and cholesterol, and the pulmonary infection is a result of cystic fibrosis. In a further embodiment, the weight ratio is about 3:1 to about 1:1, 2:1 to about 1:1, or about 1:1.

In another embodiment, the present invention relates to the aforementioned method of treating, wherein the antiinfective is amikacin, the weight ratio of lipid to antiinfective is about 4:1 to about 0.5:1, the lipid formulation comprises DPPC and cholesterol, and the liposome has a mean diameter of about 0.1 μm to about 0.5 μm. In a further embodiment, the mean diameter is about 0.2 μm to about 0.4 μm, or about 0.2 μm to about 0.3 μm.

In another embodiment, the present invention relates to the aforementioned method of treating, wherein the antiinfective is amikacin, the weight ratio of lipid to antiinfective is about 4:1 to about 0.5:1, the lipid formulation comprises DPPC and cholesterol, the pulmonary infection is the result of cystic fibrosis, and the liposome has a mean diameter of about 0.1 μm to about 1.0 μm. In a further embodiment, the mean diameter is about 0.2 μm to about 0.5 μm, or about 0.2 μm to about 0.3 μm.

These embodiments of the present invention, other embodiments, and their features and characteristics, will be apparent from the description, drawings and claims that follow.

DETAILED DESCRIPTION

Figure 1:
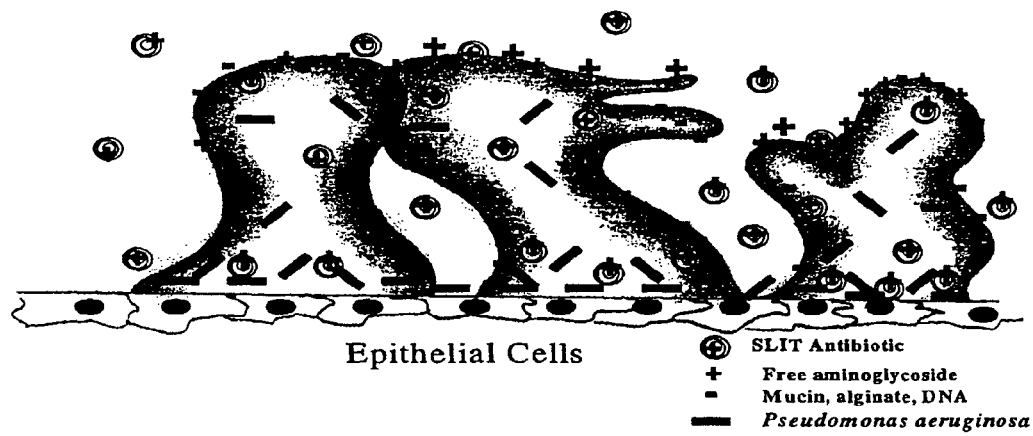
FIG. 1 depicts the cross sectional diagram of the sputum/biofilm seen in patients with cystic fibrosis.

The present invention discloses a lipid formulation comprising an antiinfective wherein the size and lipid to drug ratios are smaller than previously known. The present invention also discloses a method of preparing these lipid formulations.

1. Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e. to at least one) of the grammatical object of the article. By way of example, "an element" means one element or more than one element.

The term "bioavailable" is art-recognized and refers to a form of the subject invention that allows for it, or a portion of the amount administered, to be absorbed by, incorporated to, or otherwise physiologically available to a subject or patient to whom it is administered.

The terms "comprise" and "comprising" are used in the inclusive, open sense, meaning that additional elements may be included.

The terms "encapsulated" and "encapsulating" are refers to adsorption of antiinfectives on the surface of lipid based formulation, association of antiinfectives in the interstitial region of bilayers or between two monolayers, capture of antiinfectives in the space between two bilayers, or capture of antiinfectives in the space surrounded by the inner most bilayer or monolayer.

The term "including" is used herein to mean "including but not limited to". "Including" and "including but not limited to" are used interchangeably.

The term "lipid antiinfective formulation," or "Lip-antiinfective," or "Lip-An" discussed herein is any form of antiinfective composition where at least about 1% by weight of the antiinfective is associated with the lipid either as part of a complex with the lipid, or as a liposome where the antibiotic may be in the aqueous phase or the hydrophobic bilayer phase or at the interfacial headgroup region of the liposomal bilayer. Preferably, at least about 5%, or at least about 10%, or at least about 20%, or at least about 25%, can be so associated. Association can be measured by separation through a filter where lipid and lipid-associated antiinfective is retained and free antiinfective is in the filtrate. A "liposomal antiinfective formulation" is a lipid antiinfective formulation wherein the lipid formulation is the form of a liposome.

The term "mammal" is known in the art, and exemplary mammals include humans, primates, bovines, porcines, canines, felines, and rodents (e.g., mice and rats).

A "patient," "subject" or "host" to be treated by the subject method may mean either a human or non-human animal.

The term "pharmaceutically-acceptable salts" is art-recognized and refers to the relatively non-toxic, inorganic and organic acid addition salts of compounds, including, for example, those contained in compositions of the present invention.

The term "solvent infusion" is a process that includes dissolving one or more lipids in a small, preferably minimal, amount of a process compatible solvent to form a lipid suspension or solution (preferably a solution) and then adding the solution to an aqueous medium containing bioactive agents. Typically a process compatible solvent is one that can be washed away in a aqueous process such as dialysis. The composition that is cool/warm cycled is preferably formed by solvent infusion, with ethanol infusion being preferred. Alcohols are preferred as solvents. "Ethanol infusion," a type of solvent infusion, is a process that includes dissolving one or more lipids in a small, preferably minimal, amount of ethanol to form a lipid solution and then adding the solution to an aqueous medium containing bioactive agents. A "small" amount of solvent is an amount compatible with forming liposomes or lipid complexes in the infusion process. The term "solvent infusion" may also include an in-line infusion process where two streams of formulation components are first mixed in-line.

The term "substantially free" is art recognized and refers to a trivial amount or less.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The phrase "therapeutically effective amount" as used herein means that amount of a compound, material, or composition comprising a lipid antiinfective formulation according to the present invention which is effective for producing some desired therapeutic effect by inhibiting pulmonary infections.

The term "treating" is art-recognized and refers to curing as well as ameliorating at least one symptom of any condition or disease. The term "treating" also refers to prophylactic treating which acts to defend against or prevent a condition or disease.

2. Antiinfectives

Antiinfectives are agents that act against infections, such as bacterial, mycobacterial, fungal, viral or protozoal infections. Antiinfectives covered by the invention include but are not limited to aminoglycosides (e.g., streptomycin, gentamicin, tobramycin, amikacin, netilmicin, kanamycin, and the like), tetracyclines (such as chlortetracycline, oxytetracycline, methacycline, doxycycline, minocycline and the like), sulfonamides (e.g., sulfanilamide, sulfadiazine, sulfamethaoxazole, sulfisoxazole, sulfacetamide, and the like), paraaminobenzoic acid, diaminopyrimidines (such as trimethoprim, often used in conjunction with sulfamethoxazole, pyrazinamide, and the like), quinolones (such as nalidixic acid, cinoxacin, ciprofloxacin and norfloxacin and the like), penicillins (such as penicillin G, penicillin V, ampicillin, amoxicillin, bacampicillin, carbenicillin, carbenicillin indanyl, ticarcillin, azlocillin, mezlocillin, piperacillin, and the like), penicillinase resistant penicillin (such as methicillin, oxacillin, cloxacillin, dicloxacillin, nafcillin and the like), first generation cephalosporins (such as cefadroxil, cephalexin, cephradine, cephalothin, cephapirin, cefazolin, and the like), second generation cephalosporins (such as cefaclor, cefamandole, cefonicid, cefoxitin, cefotetan, cefuroxime, cefuroxime axetil; cefmetazole, cefprozil, loracarbef, ceforanide, and the like), third generation cephalosporins (such as cefepime, cefoperazone, cefotaxime, ceftizoxime, ceftriaxone, ceftazidime, cefixime, cefpodoxime, ceftibuten, and the like), other beta-lactams (such as imipenem, meropenem, aztreonam, clavulanic acid, sulbactam, tazobactam, and the like), beta-lactamase inhibitors (such as clavulanic acid), chlorampheriicol, macrolides (such as erythromycin, azithromycin, clarithromycin, and the like), lincomycin, clindamycin, spectinomycin, polymyxin B, polymixins (such as polymyxin A, B, C, D, E1(colistin A), or E2, colistin B or C, and the like) colistin, vancomycin, bacitracin, isoniazid, rifampin, ethambutol, ethionamide, aminosalicylic acid, cycloserine, capreomycin, sulfones (such as dapsone, sulfoxone sodium, and the like), clofazimine, thalidomide, or any other antibacterial agent that can be lipid encapsulated. Antiinfectives can include antifungal agents, including polyene antifungals (such as amphotericin B, nystatin, natamycin, and the like), flucytosine, imidazoles (such as n-ticonazole, clotrimazole, econazole, ketoconazole, and the like), triazoles (such as itraconazole, fluconazole, and the like), griseofulvin, terconazole, butoconazole ciclopirax, ciclopirox olamine, haloprogin, tolnaftate, naftifine, terbinafine, or any other antifungal that can be lipid encapsulated or complexed. Discussion and the examples are directed primarily toward amikacin but the scope of the application is not intended to be limited to this antiinfective. Combinations of drugs can be used.

Particularly preferred antiinfectives include the aminoglycosides, the quinolones, the polyene antifungals and the polymyxins.

Also included as suitable antiinfectives used in the lipid antiinfective formulations of the present invention are pharmaceutically acceptable addition salts and complexes of antiinfectives. In cases wherein the compounds may have one or more chiral centers, unless specified, the present invention comprises each unique racernic compound, as well as each unique nonracemic compound.

In cases in which the antiinfectives have unsaturated carbon-carbon double bonds, both the cis (Z) and trans (E) isomers are within the scope of this invention. In cases wherein the antiinfectives may exist in tautomeric forms, such as keto-enol tautomers, such as

and

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included as suitable antiinfectives used in the lipid antiinfective formulations of the present invention are prodrugs of the platinum compounds. Prodrugs are considered to be any covalently bonded carriers which release the active parent compound in vivo.

3. Pulmonary Infections

Among the pulmonary infections (such as in cystic fibrosis patients) that can be treated with the methods of the invention are Pseudomonas (e.g., *P. aeruginosa, P. paucimobilis, P. putida, P. fluorescens,* and *P. acidovorans*), staphylococcal, Methicillinresistant *Staphylococcus aureus* (MRSA), streptococcal (including by *Streptococcus pneumoniae*), *Escherichia coli, Klebsiella, Enterobacter, Serratia, Haemophilus, Yersinia pesos, Burkholderia pseudomallei, B. cepacia, B. gladioli, B. multivorans, B. vietnamiensis, Mycobacterium tuberculosis, M. avium* complex (MAC)(*M. avium* and *M. intracellulare*), *M. kansasii, M. xenopi, M. marinum, M. ulcerans,* or *M. fortuitum* complex (*M. fortuitum* and *M. chelonei*) infections.

4. Methods of Treatment

In one embodiment the present invention comprises a method of treatment comprising administration of a therapeutically effective amount of a lipid antiinfective formulation.

Where no specific dosage is provided below, the preferred dosage of the invention is 50% or less, 35% or less, 20% or less, or 10% or less, of the minimum free drug (which of course can be a salt) amount that is effective, if delivered to the lungs via a nebulizer, to reduce the CFU count in the lungs by one order of magnitude over the course of a 14-day treatment. The comparative free drug amount is the cumulative amount that would be used in the dosing period applied with the drug administration of the invention. The comparative minimum free drug defined in this paragraph is a "comparative free drug amount."

The non-CF treating embodiments of the invention can be used with any animal, though preferably with humans. Relative amounts in a given animal are measured with respect to such animal.

The dosing schedule is preferably once a day or less. In preferred embodiments, the dosing schedule is once every other day, every third day, every week, or less. For example, the dosing schedule can be every other day or less, using 50% or less of the comparative free drug amount. Or, for example, the dosing can be daily using 35% or less of the comparative free drug amount. See FIGS. 3 and 4 for animal data showing that the lipid antiinfective formulations of the present invention are more efficacious than the free drug.

To treat infections, the effective amount of the antiinfective will be recognized by clinicians but includes an amount effective to treat, reduce, ameliorate, eliminate or prevent one or more symptoms of the disease sought to be treated or the condition sought to be avoided or treated, or to otherwise produce a clinically recognizable change in the pathology of the disease or condition. Amelioration includes reducing the incidence or severity of infections in animals treated prophylactically. In certain embodiments, the effective amount is one effective to treat or ameliorate after symptoms of lung infection have arisen. In certain other embodiments, the effective amount is one effective to treat or ameliorate the average incidence or severity of infections in animals treated prophylactically (as measured by statistical studies).

Liposome or other lipid delivery systems can be administered for inhalation either as a nebulized spray, powder, or aerosol, or by intrathecal administration. Inhalation administrations are preferred. The overall result is a less frequent administration and an enhanced therapeutic index compared to free drug or parenteral form of the drug. Liposomes or other lipid formulations are particularly advantageous due to their ability to protect the drug while being compatible with the lung lining or lung surfactant.

The present invention includes methods for treatment of pulmonary gram-negative infections. One usefully treated infection is chronic pseudomonal infection in CF patients. Known treatments of lung infections (such as in CF patients) with aminoglycoside generally comprise administering approximately 200-600 mg of amikacin or tobramycin per day via inhalation. The present invention allows for treatment by administering, in one preferred embodiment, 100 mg or less of amikacin per day (or normalized to 100 mg per day or less if dosing less frequent). In yet another embodiment, administration of 60 mg or less of amikacin every day is performed. And in still another embodiment administration of approximately 30 to 50 mg not more than once every 2 days is performed. The most preferred embodiment comprises administration of approximately 30 to 50 mg every other day or every third day.

5. Lipids and Liposomes

The lipids used in the compositions of the present invention can be synthetic, semi-synthetic or naturally-occurring lipids, including phospholipids, tocopherols, steroids, fatty acids, glycoproteins such as albumin, anionic lipids and cationic lipids. The lipids may be anionic, cationic, or neutral. In one embodiment, the lipid formulation is substantially free of anionic lipids. In one embodiment, the lipid formulation comprises only neutral lipids. In another embodiment, the lipid formulation is free of anionic lipids. In another embodiment, the lipid is a phospholipid. Phosholipids include egg phosphatidylcholine (EPC), egg phosphatidylglycerol (EPG), egg phosphatidylinositol (EPI), egg phosphatidylserine (EPS), phosphatidylethanolamine (EPE), and egg phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid can be made up of fatty acids of different chain lengths and different degrees of unsaturation. In particular, the compositions of the formulations can include dipalmitoylphosphatidylcholine (DPPC), a major constituent of naturally-occurring lung surfactant as well as dioleoylphosphatidylcholine (DOPC). Other examples include dimyristoylphosphatidylcholine (DMPC) and dimyristoylphosphatidylglycerol (DMPG) dipalritoylphosphatidcholine (DPPC) and dipalmitoylphosphatidylglycerol (DPPG) distearoylphosphatidylcholine (DSPC) and distearoylphosphatidylglycerol (DSPG), dioleylphosphatidylethanolamine (DOPE) and mixed phospholipids like palmitoylstearoylphosphatidylcholine (PSPC) and palmitoylstearoylphosphatidylglycerol (PSPG), driacylglycerol, diacylglycerol, seranide, sphingosine, sphingomyelin and single acylated phospholipids like mono-oleoyl-phosphatidylethanol amine (MOPE).

The lipids used can include ammonium salts of fatty acids, phospholipids and glycerides, steroids, phosphatidylglycerols (PGs), phosphatidic acids (PAs), phosphotidylcholines (PCs), phosphatidylinositols (PIs) and the phosphatidylserines (PSs). The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9 (Z)-octadecenyloxy)-prop-1-yl-N,N,N-trimethylammonium chloride (DOTMA) and 1,2-bis(oleoyloxy)-3-(trimethylammonio)propane (DOTAP). Examples of steroids include cholesterol and ergosterol. Examples of PGs, PAs, PIs, PCs and PSs include DMPG, DPPG, DSPG, DMPA, DPPA, DSPA, DMPI, DPPI, DSPI, DMPS, DPPS and DSPS, DSPC, DPPG, DMPC, DOPC, egg PC.

Liposomes or lipid antiinfective formulations composed of phosphatidylcholines, such as DPPC, aid in the uptake by the cells in the lung such as the alveolar macrophages and helps to sustain release of the antiinfective agent in the lung (Gonzales-Rothi et al. (1991)). The negatively charged lipids such as the PGs, PAs, PSs and PIs, in addition to reducing particle aggregation, can play a role in the sustained release characteristics of the inhalation formulation as well as in the transport of the formulation across the lung (transcytosis) for systemic uptake. The sterol compounds are believed to affect the release and leakage characteristics of the formulation.

Liposomes are completely closed lipid bilayer membranes containing an entrapped aqueous volume. Liposomes can be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase. Lipid antiinfective formulations are associations lipid and the antiinfective agent. This association can be covalent, ionic, electrostatic, noncovalent, or steric. These complexes are non-liposomal and are incapable of entrapping additional water soluble solutes. Examples of such complexes include lipid complexes of amphotencin B (Janoff et al., Proc. Nat Acad. Sci., 85:6122 6126, 1988) and cardiolipin complexed with doxorubicin.

A lipid clathrate is a three-dimensional, cage-like structure employing one or more lipids wherein the structure entraps a bioactive agent. Such clathrates are included in the scope of the present invention.

Proliposomes are formulations that can become liposomes or lipid complexes upon coming in contact with an aqueous liquid. Agitation or other mixing can be necessary. Such proliposomes are included in the scope of the present invention.

Liposomes can be produced by a variety of methods (for example, see, Bally, Cullis et al., Biotechnol Adv. 5(1): 194, 1987). Bangham's procedure (J. Mol. Biol., J Mol Biol. 13(1):238-52, 1965) produces ordinary multilamellar vesicles (MLVs). Lenk et al. (U.S. Pat. Nos. 4,522,803, 5,030, 453 and 5,169,637), Fountain et al. (U.S. Pat. No. 4,588,578) and Cullis et al. (U.S. Pat. No. 4,975,282) disclose methods for producing multilamellar liposomes having substantially equal interlamellar solute distribution in each of their aqueous compartments. Paphadjopoulos et al., U.S. Pat. No. 4,235,871, discloses preparation of oligolamellar liposomes by reverse phase evaporation.

Unilamellar vesicles can be produced from MLVs by a number of techniques, for example, the extrusion of Cullis et al. (U.S. Pat. No. 5,008,050) and Loughrey et al. (U.S. Pat. No. 5,059,421). Sonication and homogenization can be used to produce smaller unilamellar liposomes from larger liposomes (see, for example, Paphadjopoulos et al., Biochim. Biophys. Acta., 135:624-638, 1967; Deamer, U.S. Pat. No. 4,515,736; and Chapman et al., Liposome Technol., 1984, pp. 1-18).

The original liposome preparation of Bangham et al. (J. Mol. Biol., 1965, 13:238-252) involves suspending phospholipids in an organic solvent which is then evaporated to dryness leaving a phospholipid film on the reaction vessel. Next, an appropriate amount of aqueous phase is added, the mixture is allowed to "swell", and the resulting liposomes which consist of multilamellar vesicles (MLVs) are dispersed by mechanical means. This preparation provides the basis for the development of the small sonicated unilamellar vesicles described by Papahadjopoulos et al. (Biochim. Biophys, Acta., 1967, 135:624-638), and large unilamellar vesicles.

Techniques for producing large unilamellar vesicles (LUVs), such as, reverse phase evaporation, infusion procedures, and detergent dilution, can be used to produce liposomes. A review of these and other methods for producing liposomes can be found in the text Liposomes, Marc Ostro, ed., Marcel Dekker, Inc., New York, 1983, Chapter 1, the pertinent portions of which are incorporated herein by reference. See also Szoka, Jr. et al., (1980, Ann. Rev. Biophys. Bioeng., 9:467), the pertinent portions of which are also incorporated herein by reference.

Other techniques that are used to prepare vesicles include those that form reverse-phase evaporation vesicles (REV), Papahadjopoulos et al., U.S. Pat. No. 4,235,871. Another class of liposomes that can be used are those characterized as having substantially equal lamellar solute distribution. This class of liposomes is denominated as stable plurilamellar vesicles (SPLV) as defined in U.S. Pat. No. 4,522,803 to Lenk, et al. and includes monophasic vesicles as described in U.S. Pat. No. 4,588,578 to Fountain, et al. and frozen and thawed multilamellar vesicles (FATMLV) as described above.

A variety of sterols and their water soluble derivatives such as cholesterol hemisuccinate have been used to form liposomes; see specifically Janoff et al., U.S. Pat. No. 4,721,612, issued Jan. 26, 1988, entitled "Steroidal Liposomes." Mayhew et al, described a method for reducing the toxicity of antibacterial agents and antiviral agents by encapsulating them in liposomes comprising alpha-tocopherol and certain derivatives thereof. Also, a variety of tocopherols and their water soluble derivatives have been used to form liposomes, see Janoff et al., U.S. Pat. No. 5,041,278.

6. Methods of Preparation

A process for forming liposomes or lipid antiinfective formulations involves a "solvent infusion" process. This is a process that includes dissolving one or more lipids in a small, preferably minimal, amount of a process compatible solvent to form a lipid suspension or solution (preferably a solution) and then infusing the solution into an aqueous medium containing the antiinfective. Typically a process compatible solvent is one that can be washed away in a aqueous process such as dialysis or diafiltration. "Ethanol infusion," a type of solvent infusion, is a process that includes dissolving one or more lipids in a small, preferably minimal, amount of ethanol to form a lipid solution and then infusing the solution into an aqueous medium containing the antiinfective. A "small" amount of solvent is an amount compatible with forming liposomes or lipid complexes in the infusion process. Such processes are described in Lee et al., U.S. patent application Ser. No. 10/634,144, filed Aug. 4, 2003, Pilkiewicz et al, U.S. patent application Ser. No. 10/383,173, filed Mar. 5, 2003, and Boni et al., U.S. patent application Ser. No. 10/383,004, filed Mar. 5, 2003, which applications are hereby incorporated by reference in their entirety.

The step of infusing the lipid-alcohol solution into the aqueous or alcoholic solution or mixture containing the antiinfective can be performed above or below the surface of the aqueous or alcoholic solution or mixture containing the antiinfective. Preferably, the step is performed above the surface of the solution or mixture.

Liposomes can also be prepared by the methods disclosed in copending U.S. patent applications Ser. No. 10/383,004, filed Mar. 5, 2003; Ser. No. 10/634,144, filed Aug. 4, 2003; Ser. No. 10/224,293, filed Aug. 20, 2002; and Ser. No. 10/696, 389, filed Oct. 29, 2003, the specifications of which are incorporated herein in their entirety.

Liposome or lipid formulation sizing can be accomplished by a number of methods, such as extrusion, sonication and homogenization techniques which are well known, and readily practiced, by ordinarily skilled artisans. Extrusion involves passing liposomes, under pressure, one or more times through filters having defined pore sizes. The filters are generally made of polycarbonate, but the filters may be made of any durable material which does not interact with the liposomes and which is sufficiently strong to allow extrusion under sufficient pressure. Preferred filters include "straight through" filters because they generally can withstand the higher pressure of the preferred extrusion processes of the present invention. "Tortuous path" filters may also be used. Extrusion can also use asymmetric filters, such as Anopore™ filters, which involves extruding liposomes through a branched-pore type aluminum oxide porous filter.

Liposomes or lipid formulations can also be size reduced by sonication, which employs sonic energy to disrupt or shear liposomes, which will spontaneously reform into smaller liposomes. Sonication is conducted by immersing a glass tube containing the liposome suspension into the sonic epicenter produced in a bath-type sonicator. Alternatively, a probe type sonicator may be used in which the sonic energy is generated by vibration of a titanium probe in direct contact with the liposome suspension. Homogenization and milling apparatii, such as the Gifford Wood homogenizer, Polytron™ or Microfluidizer, can also be used to break down larger liposomes or lipid formulations into smaller liposomes or lipid formulations.

The resulting liposomal formulations can be separated into homogeneous populations using methods well known in the art; such as tangential flow filtration. In this procedure, a heterogeneously sized population of liposomes or lipid formulations is passed through tangential flow filters, thereby resulting in a liposome population with an upper and/or lower size limit. When two filters of differing sizes, that is, having different pore diameters, are employed, liposomes smaller than the first pore diameter pass through the filter. This filtrate can the be subject to tangential flow filtration through a second filter, having a smaller pore size than the first filter. The retentate of this filter is a liposomal/complexed population having upper and lower size limits defined by the pore sizes of the first and second filters, respectively.

Mayer et al. found that the problems associated with efficient entrapment of lipophilic ionizable bioactive agents such as antineoplastic agents, for example, anthracyclines or vinca alkaloids, can be alleviated by employing transmembrane ion gradients. Aside from inducing greater uptake, such transmembrane gradients can also act to increase antiinfective retention in the liposomal formulation.

Lipid antiinfective formulations have a sustained antiinfective effect and lower toxicity allowing less frequent administration and an enhanced therapeutic index. In preclinical animal studies and in comparison to inhaled tobramycin (not-liposomal or lipid-based) at the equivalent dose level, liposomal amikacin was shown to have, during the time period shortly after administration to over 24 hours later, drug levels in the lung that ranged from two to several hundred times that of tobramycin. Additionally, liposomal amikacin maintained these levels for well over 24 hours. In an animal model designed to mimic the pseudomonas infection seen in CF patients, liposomal amikacin was shown to significantly eliminate the infection in the animals' lungs when compared to free aminoglycosides.

Lung surfactant allows for the expansion and compression of the lungs during breathing. This is accomplished by coating the lung with a combination of lipid and protein. The lipid is presented as a monolayer with the hydrophobic chains directed outward. The lipid represents 80% of the lung surfactant, the majority of the lipid being phosphatidylcholine, 50% of which is dipalmitoyl phosphatidylcholine (DPPC) (Veldhuizen et al, 1998). The surfactant proteins (SP) that are present function to maintain structure and facilitate both expansion and compression of the lung surfactant as occurs during breathing. Of these, SP-B and SP-C specifically have lytic behavior and can lyse liposomes (Hagwood et al., 1998; Johansson, 1998). This lytic behavior could facilitate the gradual break-up of liposomes. Liposomes can also be directly ingested by macrophages through phagocytosis (Couveur et al., 1991; Gonzales-Roth et al., 1991; Swenson et al, 1991). Uptake of liposomes by alveolar macrophages is another means by which drugs can be delivered to the diseased site.

The lipids preferably used to form either liposomal or lipid formulations for inhalation are common to the endogenous lipids found in the lung surfactant. Liposomes are composed of bilayers that entrap the desired pharmaceutical. These can be configured as multilamellar vesicles of concentric bilayers with the pharmaceutical trapped within either the lipid of the different layers or the aqueous space between the layers. The present invention utilizes unique processes to create unique liposomal or lipid antiinfective formulations. Both the processes and the product of these processes are part of the present invention.

6.1 In-Line Infusion Method

Figure 8:
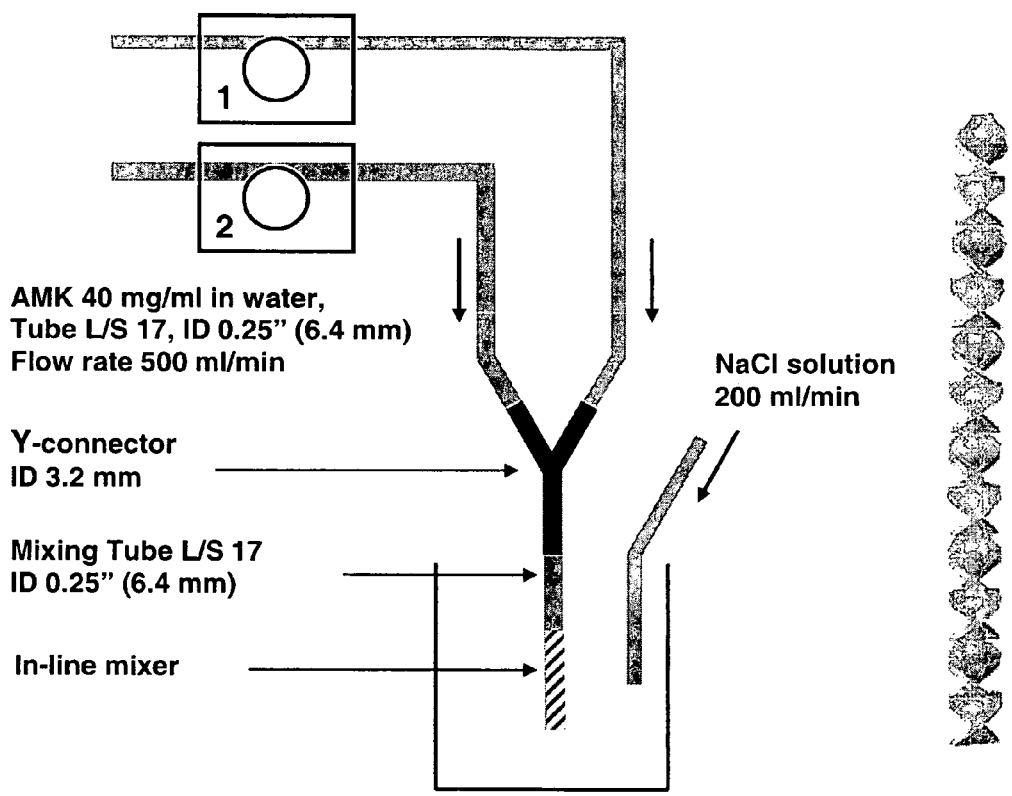
FIG. 8 depicts graphically the two-stream in-line infusion process of preparing liposomal antiinfective formulations.

In one particularly preferred embodiment, the liposomal antiinfective formulations of the present invention are prepared by an in-line infusion method where a stream of lipid solution is mixed with a stream of antiinfective solution in-line. For example, the two solutions may be mixed in-line inside a mixing tube preceded by a Y-connector as depicted in FIG. 8. In this way, the in-line infusion method differs from the infusion method described above, where the lipid solution is infused as a stream into a bulk of antiinfective solution. Surprisingly, this infusion method results in lower lipid to drug ratios and higher encapsulation efficiencies. The process may be further improved by optimizing parameters such as flow rate, temperature, antiinfective concentration, and salt addition after infusion step.

6.1.a Effect of Flow Rates

Individual flow rates were varied while keeping the total flow rate at 800 mL/min. To do so, two separate pumps were used set at different pumping rates. The mixed solutions were infused for 10 s into a beaker containing NaCl solution such that the final NaCl concentration was 1.5% and the final ethanol concentration did not exceed 30%. After mixing, a 1 mL aliquot was run though a Sephadex G-75 gel filtration column to separate free amikacin from encapsulated. A 1 mL fraction with highest density (determined by visual turbidity) was collected for further analysis. The results are presented in Table 1. Increasing the lipid/amikacin flow rate ratio resulted in an almost constant L/D until 300/500 mL/min. With further increase of lipid rate, L/D started to increase and particle size also started getting larger. At the same time, higher lipid flow rates gave better amikacin recovery (encapsulation efficiency) as more lipid mass was added.

TABLE 1

Effect of flow rates on amikacin encapsulation.*

| Batch | Flow rates mL/min AMK | Flow rates mL/min Lipid | AMK total mg/mL | AMK free % | Lipid mg/mL | L/D | VOL Size | AMK Recovery % |
|---|---|---|---|---|---|---|---|---|
| 1 | 600 | 200 | 1.38 | 5.3 | 1.25 | 0.91 | 289 | 14.7 |
| 2 | 550 | 250 | 1.80 | 5.1 | 1.90 | 1.06 | 305 | 17.2 |
| 3 | 500 | 300 | 2.18 | 5.2 | 2.29 | 1.05 | 314 | 22.8 |
| 4 | 450 | 350 | 1.27 | 5.8 | 1.47 | 1.16 | 388 | 26.8 |
| 5 | 400 | 400 | 1.05 | 6.1 | 1.69 | 1.61 | 471 | 24.9 |

*Lipid and amikacin solutions were kept at 40° C. Amikacin stock solution was 50 mg/mL. NaCl 10% solution was added before infusion to obtain final 1.5%. Infusion time was set at 10 s. Mixing tube 10 cm; 6-element in-line mixer positioned at 0 cm.

Batch 3 with the lipid/amikacin flow rates of 300/500 mL/min showed the best L/D and particle size, combined with reasonably high amikacin recovery. Thus it was decided to use these flow rates for all further experiments.

In order to reproduce the results at chosen conditions a fully washed batch (batch 6) using diafiltration was prepared as presented in Table 2. NaCl 10% solution was added into the beaker prior to infusion to make the final concentration 2% (as compared to 1.5% in the batches in Table 1). The resulting L/D (1.71) was not as good as in batch 3 in Table 1 and the particle size was higher. This may be due to an adverse effect of high NaCl concentration contacting liposomes in the early stages of liposome formation. Samples separated (washed) using gel-filtration columns tend to have better L/D than ones washed by diafiltration. This may have to do with the different degree of stress liposomes experience, or simply samples separated on the gel filtration column contained a fraction of liposomes with better L/D which does not represent the whole population.

TABLE 2

Summary of the fully washed batches. Process parameters varied were: temperatures, amikacin stock concentration, and other (see Table 3 below). All batches were concentrated to nearly a maximum extent, until the inlet pressure reached 10 PSI.

| Batch | Temp, C. L/AMK/W | AMK stock mg/mL | AMK total mg/mL | AMK free % | Lipid mg/mL | L/D | Size VOL nm | Size SD % |
|---|---|---|---|---|---|---|---|---|
| 6 | 40/40/30 | 50 | 36.1 | 2.7 | 61.8 | 1.71 | 392 | 43.4 |
| 8 | 50/RT/30 | 50 | 48.5 | 9.6 | 49.3 | 1.02 | 332 | 32.0 |
| 9 | 50/RT/30 | 50 | 41.6 | 5.1 | 43.2 | 1.04 | 359 | 34.4 |
| 10 | 50/RT/30 | 50 | 53.1 | 10.2 | 34.4 | 0.65 | 350 | 28.6 |
| 11 | 50/RT/30 | 40 | 20.7 | 4.8 | 46.9 | 2.27 | 407 | 35.9 |
| 12 | 50/RT/30 | 40 | 81.0 | 1.9 | 49.4 | 0.61 | 341 | 33.0 |
| 13 | 50/RT/30 | 30 | 68.6 | 1.7 | 62.5 | 0.91 | 311 | 22.4 |
| 14 | 50/RT/30 | 40 | 79.6 | 1.6 | 47.8 | 0.60 | 346 | 37.2 |
| 15 | 50/RT/30 | 40 | 71.3 | 2.0 | 42.3 | 0.59 | 353 | 33.4 |
| 16 | 30/30/30 | 40 | 61.9 | 6.1 | 51.5 | 0.83 | 369 | 28.4 |
| 17 | 30/30/30 | 40 | 73.8 | 2.4 | 57.2 | 0.77 | 362 | 32.6 |
| 18 | 30/30/30 | 40 | 74.4 | 2.3 | 54.0 | 0.73 | 549 | 61.7 |

*The 3$^{rd}$ column represents the temperatures of Lipid and Amikacin solutions just before infusion, and the temperature during washing (diafiltration).
RT = room temperature.
"VOL size" is the volume weighted particle size.

TABLE 3

Processing conditions for batches 1-18.*

| Batch | Mixing tube cm | Mixer position cm | NaCl added Stock % | Volume parts | Timing to infusion | Washing condition NaCl % | 1st wash |
|---|---|---|---|---|---|---|---|
| 1-5 | 10 | 0 | VAR | VAR | before | 1.5 | (Seph column) |
| 6 | 10 | 0 | 10 | 200 | before | 1.5 | diafiltration |
| 7 | 10 | 5 | 10 | 100 | before | 1.5 | (Seph column) |
| 8 | 10 | 5 | 10 | 150 | during | 1.5 | diafiltration |
| 9 | 10 | 5 | 10 | 150 | during | 1.5 | diafiltration |
| 10 | 10 | 5 | 10 | 100 | 5' after | 1.5 | 2× dilution |
| 11 | 10 | 5 | 10 | 150 | imm after | 1.5 | 2× dilution |
| 12 | 10 | 5 | H2O | 180 | 20" after | 1.5 | 2× dilution |
| 13 | 10 | 5 | H2O | 180 | 30" after | 1.5 | 2× dilution |
| 14 | 10 | 5 | H2O | 180 | 30" after | 1.5 | diafiltration |
| 15 | 10 | 5 | 1.5 | 180 | 30" after | 1.5 | diafiltration |
| 16 | 60 | NO | 0.9 | 180 | during | 0.9 | diafiltration |
| 17 | 60 | NO | 1.5 | 180 | during | 1.5 | diafiltration |
| 18 | 60 | 0 | 1.5 | 180 | during | 1.5 | diafiltration |

*Lipid and amikacin solutions were infused at rates 300/500 mL/min for 30 s (examples 6-10) or 20 s (examples 11-18). Additional aqueous solution (NaCl or water) was added (as parts relative to 500 parts amikacin volume).

6.1.b Effects of Process Temperature.

The settings were kept the same as in batch 3 except that the amount of NaCl solution added was less, making the final concentration 1.0%. Solution was added again before infusion was initiated because with the short infusion time it was difficult to make the addition during infusion. Also, during infusion the in-line mixer shifted to the end of the mixing tube under the pressure of the flow. The position of the mixer was 5 cm from the front end of the tube instead of 0 cm for batch 3. This may be important, as the L/D ratio obtained at the same temperature 40/40° C. condition in batch 20 was 0.55, almost half of that in batch 3. On comparing amikacin encapsulation at different infusion temperatures, one can see that, surprisingly, lower temperatures gave better L/D. Of the temperatures tested, lipid/amikacin temperatures 30/30° C. and 50/RT gave similar L/D ratios of 0.32 and 0.37. Again, as in batches 1-5, the numbers from these washed samples by gel-filtration were low, perhaps less than that if the batches had been washed by diafiltration.

TABLE 4

Effect of temperature on amikacin encapsulation.*

| Batch | Temperature, C. Lipid | AMK | AMK total mg/mL | AMK free % | Lipid mg/mL | L/D | VOL Size nm |
|---|---|---|---|---|---|---|---|
| 19 | 30 | 30 | 4.88 | 2.8 | 1.54 | 0.32 | 278 |
| 20 | 40 | 40 | 3.62 | 1.5 | 1.98 | 0.55 | 335 |
| 21 | 50 | 50 | 3.50 | 1.8 | 2.74 | 0.78 | 309 |
| 22 | 50 | RT | 5.27 | 2.9 | 1.93 | 0.37 | 342 |

*Lipid and amikacin solutions were infused at rates 300/500 mL/min for 10 s. Amikacin stock solution was 50 mg/mL. NaCl 10% solution was added before infusion to obtain a final 1.0% concentration. Mixing tube 10 cm, 6-element in-line mixer positioned at 5 cm.

In separate experiments it was found that mixing of 90% ethanol and water at either 30° C. and 30° C. or 50° C. and 22° C., respectively, resulted in a similar final temperature of nearly 36° C. This suggests that the temperature of the final mixture rather than that of the individual components is important for amikacin encapsulation. The temperatures 50° C./RT were used in examples 6-15. In examples 16-18 temperatures of 30° C. and 30° C. for the two streams were used with comparable results, although a little less amikacin encapsulation was observed.

6.1.c. Effect of Post-infusion Addition of Aqueous Volume

Attention was next focused on the steps of NaCl solution addition and the washing process. Process parameters were varied in various directions. Right after the infusion step at flow rates 300/500, ethanol concentration in the mixture reaches 34%. Amikacin has limited solubility at this concentration (see FIG. 9).

Figure 9:
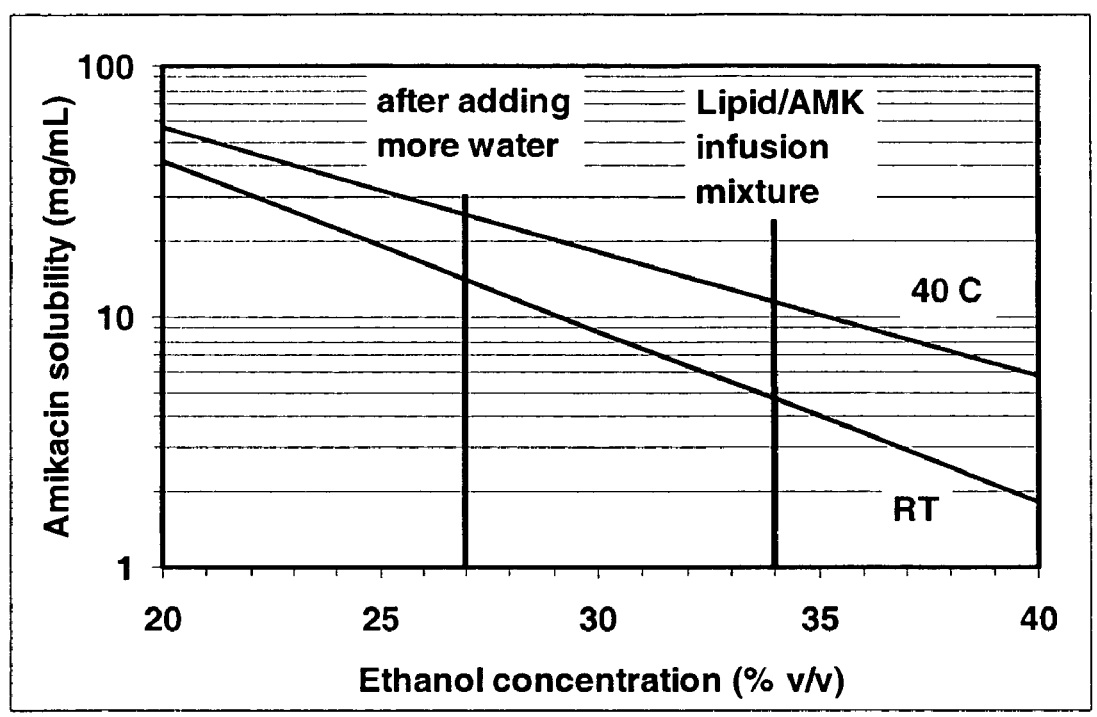
FIG. 9 depicts miscibility of amikacin sulfate with ethanol/water. Lines represent maximal amikacin concentration (base) miscible with ethanol solution at room temperature (RT) and 40° C. At higher concentrations amikacin forms a separate liquid phase (coacervates), which later precipitates as crystals. Vertical lines show ethanol concentration in the lipid/amikacin infusion mixture (300/500 parts) and after adding water 200 parts.

If one starts with 50 mg/mL amikacin stock, then after mixing with the lipid solution there will be more than 30 mg/mL total amikacin where at least half (15 mg/mL) is free amikacin, assuming 50% encapsulation efficiency. This is higher than the solubility limit at 34% ethanol. One possible solution to this problem is to add more water to the vessel with the lipid/amikacin mixture, thus reducing both ethanol and amikacin concentration. For example, adding 200 parts of water (or NaCl solution) to 800 parts of lipid/amikacin would reduce ethanol to 27% (FIG. 9). This makes amikacin soluble at 15 mg/mL or even higher depending on temperature.

In addition, adding NaCl may stabilize osmotic conditions. When liposomes are formed and amikacin is encapsulated at an internal concentration of 200-300 mg/mL, there is only ~15 mg/mL or so of amikacin not encapsulated. In the absence of saline this would create an osmotic imbalance, which in turn might lead to leakage of amikacin. Adding 150 parts of 10% NaCl to 800 parts of lipid/amikacin will result in about 1.5% NaCl final concentration (outside liposomes).

A number of batches were generated where different amounts of NaCl solution (or water in some batches) were added at different times relative to the infusion event (see Table 5, compiled from Tables 2 and 3). From the table a general trend can be seen, leading to the following conclusions:

- Some time interval between infusion and addition of the aqueous volume is required to obtain lower L/D (if a short mixing tube is used). Of batches 6-15, those with an interval 20 s or longer had lower L/D. One possible explanation is that liposomes are not completely formed immediately after mixing of the streams. When a longer mixing tube is used (batches 16-18), which allows for a longer mixing time, the time interval is not required.
- Adding a high concentration NaCl solution to balance osmolality does not actually help retain amikacin. In fact, adding pure water at an appropriate time interval resulted in the lowest L/D and total amikacin concentration.
- Adding 100 parts NaCl 10% (batch 9) 5 min after infusion gave a competitive L/D ratio but did not give as good a total amikacin concentration. It may be that NaCl, when present at early stages with relatively high ethanol concentrations, leads to increased aggregation and viscosity.

TABLE 5

Role of aqueous volume and NaCl concentration added to the lipid/amikacin mixture to adjust ethanol concentration. Not all the variables shown; see Tables 2 and 3.

| Batch | AMK stock mg/mL | NaCl added Stock % | Volume parts | Timing to infusion | AMK total mg/mL | L/D | Size VOL nm |
|---|---|---|---|---|---|---|---|
| 6 | 50 | 10 | 200 | before | 36.1 | 1.71 | 392 |
| 8 | 50 | 10 | 150 | during | 48.5 | 1.02 | 332 |
| 9 | 50 | 10 | 150 | during | 41.6 | 1.04 | 359 |
| 10 | 50 | 10 | 100 | 5' after | 53.1 | 0.65 | 350 |
| 11 | 40 | 10 | 150 | imm after | 20.7 | 2.27 | 407 |
| 12 | 40 | $H_2O$ | 180 | 20" after | 81.0 | 0.61 | 341 |
| 13 | 30 | $H_2O$ | 180 | 30" after | 68.6 | 0.91 | 311 |
| 14 | 40 | $H_2O$ | 180 | 30" after | 79.6 | 0.60 | 346 |
| 15 | 40 | 1.5 | 180 | 30" after | 71.3 | 0.59 | 353 |
| 16 | 40 | 0.9 | 180 | during | 61.9 | 0.83 | 369 |
| 17 | 40 | 1.5 | 180 | during | 73.8 | 0.77 | 362 |
| 18 | 40 | 1.5 | 180 | during | 74.4 | 0.73 | 549 |

6.1.d. Effect of Antiinfective Stock Solution

Previously it was found that using 50 mg/mL amikacin stock solution produced the best entrapment. Reducing the amikacin stock concentration to 40 mg/mL increased L/D when used in conventional processes. With the two-stream in-line infusion process, ethanol concentration reaches higher levels, so the current 50 mg/mL amikacin may not be the optimal concentration.

Table 6 summarizes the effect of using various amikacin stock concentrations. 40 mg/mL delivered comparable or better L/D values, and even improved amikacin recovery. Using less amikacin relative to a constant amount of lipid, and providing a similar L/D, resulted in a higher percent encapsulation (batch 12). Further decrease of amikacin stock concentration to 30 mg/mL resulted in a slightly increased L/D, although recovery was still impressive (batch 13).

TABLE 6

Amikacin stock concentration can be reduced while improving efficiency. Amikacin recovery is calculated based on L/D obtained and assumed 100% lipid recovery.

| Batch | AMK stock mg/mL | AMK total mg/mL | AMK free % | Lipid mg/mL | L/D | Size VOL nm | AMK Recovery % |
|---|---|---|---|---|---|---|---|
| 10 | 50 | 53.1 | 10.2 | 34.4 | 0.65 | 350 | 37.0 |
| 12 | 40 | 81.0 | 1.9 | 49.4 | 0.61 | 341 | 51.2 |
| 13 | 30 | 68.6 | 1.7 | 62.5 | 0.91 | 311 | 45.7 |
| 14 | 40 | 79.6 | 1.6 | 47.8 | 0.60 | 346 | 52.0 |

Reducing amikacin stock concentration has another implication. It reduces the concentration of free amikacin in a post-infusion lipid/amikacin mixture, allowing it to remain soluble at higher ethanol concentration. Assuming that lipid and amikacin are mixed at 300/500 ratio, amikacin stock is 50 mg/mL, and encapsulation efficiency is 37%, then initial free amikacin would be ~20 mg/mL. Similarly, 40 mg/mL amikacin stock with 52% encapsulation would result in ~12 mg/mL free amikacin. 30 mg/mL amikacin stock with 46% encapsulation would result in ~10 mg/mL free amikacin.

7. Lipid to Drug Ratio

There are several ways to increase the entrapment of antiinfectives (e.g. aminoglycosides such as amikacin, tobramycin, gentamicin) in liposomes. One way is to make very large liposomes (>1 µm) where the entrapped volume per amount of lipid is large. This approach to achieve a smaller L/D ratio is not practical for inhalation (nebulization) of liposomes because 1) shear stress during nebulization tends to rupture liposomes in a size dependent manner where larger liposomes (>0.5 µm) suffer greater release and 2) the smaller droplet sizes necessary for good lung deposition are themselves less than about ~3 µm. So for inhalation, it is desirable to keep the liposome size as small as possible to avoid too much release. Currently, the mean diameter for the liposomes disclosed herein is less than about 0.4 μm (see Table 4).

Another approach to decrease L/D is to use negatively charged lipids. The aminoglycosides listed above are highly positively charged with 4 to 5 amines per compound. Usually sulfate salts of these aminoglycosides are used in therapeutic formulations. Along with the multi-cationic character comes strong binding to negatively charged liposomes. This results in greater entrapment during liposome formation. The purpose of antiinfective formulations is to provide sustained release to the lung environment. Rapid clearance of the liposomes by macrophage uptake would run counter to this. It has been well documented that negatively charged liposomes experience a much higher degree of uptake by macrophages than neutral liposomes. Therefore, it is desirable to use neutral liposomes.

One group of technologies that allow very high drug entrapment into small liposomes is based on gradient loading where a pH gradient, ammonium sulfate gradient, or Mg-sulfate gradient are used to load amine-drugs into liposomes: see U.S. Pat. Nos. 5,578,320 5,736,155 5,837,279 5,922,350 (pH gradient); U.S. Pat. Nos. 5,837,282 5,785,987 (Mg-sulfate gradient); and U.S. Pat. No. 5,316,771 (ammonium sulfate gradient). These techniques only work for membrane permeable amines (mono-amines where neutral form is permeable like doxorubicin and daunorubicin). Gradient loading will not work for the certain antiinfectives such as aminoglycosides as they are impermeable (too large and too highly charged).

All processes described herein can be easily adapted for large scale, aseptic manufacture. The final liposome size can be adjusted by modifying the lipid composition, concentration, excipients, and processing parameters.

The lipid to drug ratio using the processes of the present invention is about 4:1 to about 1:1. In another embodiment, the lipid to drug ratio is about 3:1 to about 1:1, 2:1 to about 1:1, about 1:1 or less, about 0.75:1 or less, or about 0.5:1 or less. Further the percentage of free antiinfective, present after the product is dialyzed for a particular duration, is decreased.

8. Results 8.1. Biofilm Barriers of Pulmonary Infections

An obstacle to treating infectious diseases such as *Pseudomonas aeruginosa*, the leading cause of chronic illness in cystic fibrosis patients is drug penetration within the sputum/biofilm barrier on epithelial cells (FIG. 1). In FIG. 1, the donut shapes represent a liposomal antiinfective formulation, the "+" symbol represents free antiinfective, the "–" symbol mucin, alginate and DNA, and the solid bar symbol represents *Pseudomonas aeruginosa*. This barrier is composed of both colonized and planktonic *P. aeruginosa* embedded in alginate or exopolysaccharides from bacteria, as well as DNA from damaged leukocytes, and mucin from lung epithelial cells, all possessing a net negative charge (Costerton, et al., 1999). This negative charge binds up and prevents penetration of positively charged drugs such as aminoglycosides, rendering them biologically ineffective (Mendelman et al., 1985). Entrapment of antiinfectives within liposomal or lipid formulations could shield or partially shield the antiinfectives from non-specific binding to the sputum/biofilm, allowing for liposomal or lipid formulations (with entrapped aminoglycoside) to penetrate (FIG. 1).

Amikacin has been shown to have a high degree of resistance to bacterial enzymes, thus providing a greater percent of susceptible clinical isolates than found for other aminoglycosides including tobramycin and gentamicin (Price et al., 1976). In particular, *P. aeruginosa* isolates are far more sensitive to amikacin than other aminoglycosides while exhibiting no cross-resistance (Damaso et al., 1976).

The sustained release and depot effect of liposomal formulations of amikacin is clearly seen in FIG. 2. In this study rats were given tobramycin via intratracheal and intravenous administration. The rats were also given liposomal formulations of amikacin intratracheally at the same dose (4 mg/rat). The data show that it is only with the liposomal formulation of amikacin that a sustained release and depot effect is achieved. In fact, 24 hours after dosing, only liposomal formulations of amikacin show significant levels of the drug in the animal's lungs, while both tobramycin formulations revealed negligible levels, primarily due, it is believed to rapid systemic absorption. This greater than a hundred-fold increase of aminoglycoside in the lung for liposomal antiinfective formulations supports the idea of a sustained release liposomal formulation antiinfective that can be taken significantly less often than the currently approved TOBI® formulation (a tobramycin inhalation solution made by the Chiron Corporation, Ameryville, Calif.).

Moreover, the presence of a sputum/biofilm prevents the penetration of the free aminoglycosides due to binding of the antiinfectives to its surface (FIG. 1). Therefore, doses in excess of 1,000 gm of tobramycin/gram of lung tissue are needed to show a therapeutic effect in CF patients. This is overcome with liposomal formulations of amikacin. Thus, the therapeutic level of drug is maintained for a longer period of time in the liposomal formulations of amikacin compared to free tobramycin. This facilitation of binding and penetration could also be a means by which liposomal formulations of amikacin could significantly reduce bacterial resistance commonly seen to develop when antibacterials are present in vivo at levels below the minimum inhibitory concentration.

8.2. Pharmacokinetics

The pharmacokinetics of amikacin was determined in rats following intratracheal (IT) administration of either free tobramycin or liposomal formulations of amikacin. These data were compared to the distribution obtained in the lungs following a tail vein injection of free tobramycin. In all cases a dose of 4 mg/rat was administered. As can be seen in FIG. 2, a much larger deposition of aminoglycoside can be delivered by IT compared to injection. The depot effect of liposomal antiinfective technology is also demonstrated in that in comparison to tobramycin given either IT or IV, a greater than a hundred-fold increase in drug for liposomal formulations of amikacin still remains in the lungs twenty-four hours following administration. Thus, the therapeutic level of drug is maintained for a longer period of time in the liposomal formulations of amikacin compared to free tobramycin.

The binding of aminoglycosides to sputum of CF patients is a concern, particularly if this binding reduces the bioactivity of the antiinfective (Hunt et al., 1995). To determine whether liposomal formulations of amikacin can retain biological activity over a prolonged period of time, normal rats were administered liposomal formulations of amikacin by intratracheal instillation. This was followed by its removal at 2 or 24 hours via a bronchial alveolar lavage (BAL) to determine biological activity. Samples were concentrated by ultrafiltration followed by filtration (0.2 micron) to remove contaminating lung microbes. Amikacin concentration was determined employing a TDX instrument and biological activity determined using a Mueller Hinton broth dilution assay (*Pseudomonas aeruginosa*). The results are shown in Table 7.

TABLE 7

Results showing that liposomal formulations of amikacin retain biological activity over a prolonged period of time.

| time (hours) | amikacin in BAL (µg/mL) | amikacin in filtrate (µg/mL) | MIC (µg/mL) |
|---|---|---|---|
| 2 | 160 | 119 | 1.9 |
| 24 | 73 | 32 | 4.0 |

Figure 2:
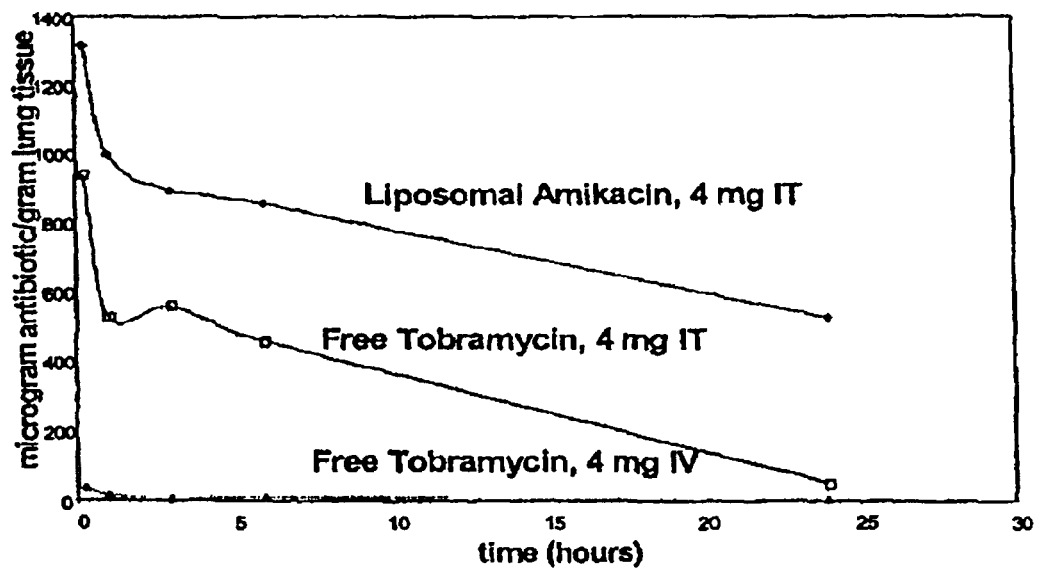
FIG. 2 depicts the graphical representation of the targeting and depot effect of the drug of the present invention.

As shown by the above table, the recovered filtered liposomal formulation of amikacin was capable of killing *P. aeruginosa* in a Mueller Hinton broth assay even after 24 hours with an MIC of 4. At 2 hours an MIC of 2 was obtained, which is similar to that obtained for the filtered liposomal/complexed amikacin stock. Thus, the liposomal formulation of amikacin was still active following 24 hours in the lung. At 24 hours free tobramycin at the same dose was undetectable in a BAL. This indicates that not only is the liposomal antiinfective formulation retained in the lung, but it is also freely available to penetrate a sputum/biofilm over time. These data combined with the facts as evident in FIG. 2 and Table 9 (below), that liposomal formulations of amikacin release the free antiinfective over time while maintaining high levels of the antiinfective in the lungs, supports the rationale that this system may yield a sustained antiinfective effect over time. This effect should prove significant in reducing both the bioburden of the *Pseudomonas* and the development of resistance due to trough levels of antiinfective.

As an in vitro demonstration of slow release of liposomal formulation of amikacin and its sustained antiinfective effect, the formulation was incubated in sputum from patients with Chronic Obstructive Pulmonary Disease (COPD) containing PAOI mucoid *Pseudomonas*. The liposomal formulation of amikacin was also incubated in alginate containing PAO1 mucoid *Pseudomonas*. In both cases sustained and enhanced killing of the *Pseudomonas* over time was observed, as shown in Table 8.

TABLE 8

In vitro killing of *Pseudomonas* over time.

In vitro Sputum/Alginate Assay (% survival of PA01 Mucoid *Pseudomonas*)

| | | Incubation time at 37° C. | | | Amikacin conc. |
|---|---|---|---|---|---|
| | | 1 h | 3 h | 6 h | 24 | (µg/mL) |
| Lip-An-15 | Sputum | 81 | 15 | 22 | <1 | 8 |
| Lip-An-15 | Alginate | 100 | 59 | 1 | <1 | 10 |

Classical kill curves are not applicable for liposomal antiinfective formulation technology because the liposomal formulations exhibit a slow release of antiinfective with an enhanced antiinfective effect. The liposomal formulation protects the amikacin from the sputum and/or alginate until its release. In time, complete killing is observed, consistent with slow release sustained antiinfective effect model with no interference or inactivation of antiinfective.

The efficacy of liposomal amikacin formulations was studied using a model for chronic pulmonary infection (Cash et al., 1979) where *P. aeruginosa*, embedded in an agarose bead matrix, was instilled in the trachea of rats. This mucoid *Pseudomonas* animal model was developed to resemble the *Pseudomonas* infections seen in CF patients. Some of the clinical correlates to CF include: a similar lung pathology; the development of immune complex disorders; and a conversion to the mucoid phenotype by *P. aeruginosa* strains (Cantin and Woods, 1999). Rat lungs were infected with over $10^7$ CFUs of a mucoid *Pseudomonas* (strain PAO1) taken from a CF patient isolate, and subsequently treated with (a) free aminoglycoside, (b) the lipid vehicle alone as non-drug control, and (c) liposomal amikacin formulation. In addition, formulations were first screened on the ability to kill in vitro *P. aeruginosa* on modified Kirby-Bauer plates.

Figure 3:
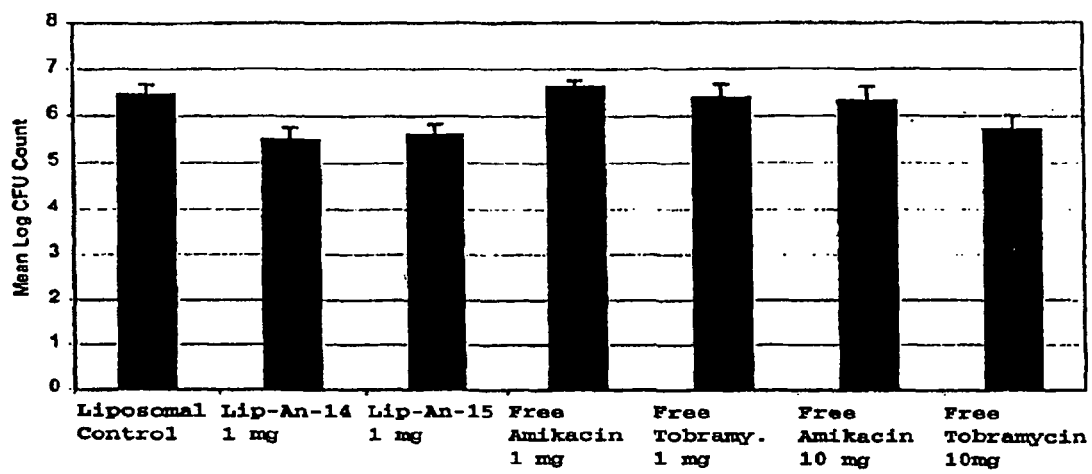
FIGS. 3 and 4 depict graphical representations of bacteriology of amikacin in various forms.
Figure 4:
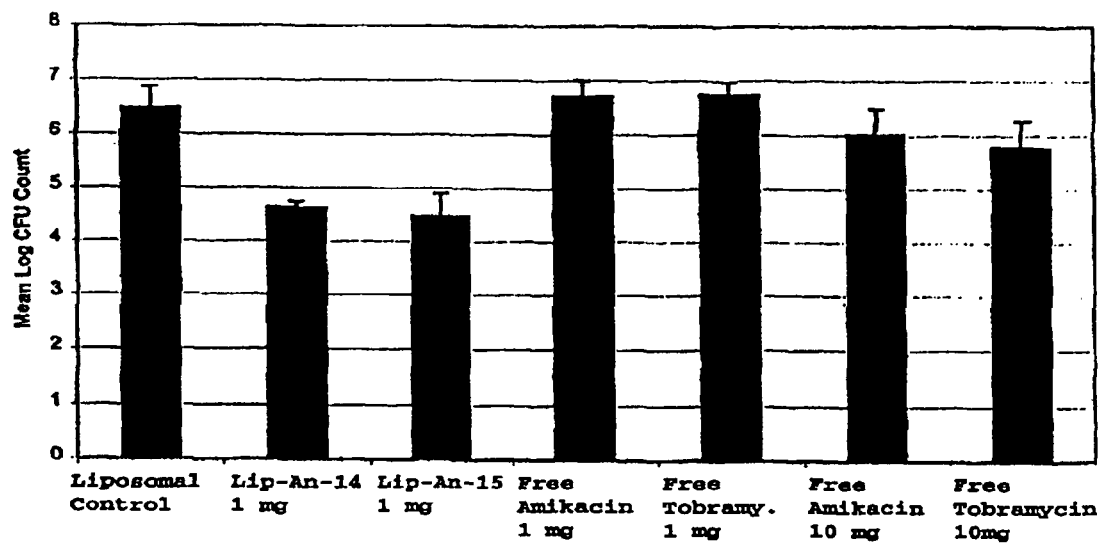

Various liposomal amikacin formulations were tested based on either different lipid compositions or manufacturing parameters resulting in different killing zones in in vitro experiments. This experiment was designed to determine the increase in efficacy obtained with liposomal aminoglycoside formulations over free aminoglycoside. Blank control lipid compositions, two different liposomal amikacin formulations and free amikacin and free Tobramycin at the same aminoglycoside concentrations as the liposomal antiinfective formulations were compared. In addition, a 10 fold higher dose of free amikacin and a 10 fold higher dose of free tobramycin were also given. Dosing was IT daily over seven days. Results (FIG. 3) indicate that liposomal amikacin in the two formulations (differing in lipid composition) revealed a significant reduction in CFU levels and were better at reducing CFUs than free amikacin or free tobramycin at 10-fold higher-dosages. In FIG. 3, Lip-An-14 is DPPC/Chol/DOPC/DOPG (42:45:4:9) and 10 mg/mL amikacin, Lip-An-15 is DDPC/Chol (1:1) also at 10 mg/mL. All lipid-lipid and lipid-drug ratios herein are weight to weight.

The next experiment (FIG. 4) was designed to demonstrate the slow release and sustained antiinfective capabilities of liposomal amikacin formulations. The dosing was every other day for 14 days, as opposed to every day for seven days as in the previous experiments. Results indicate that liposomal amikacin in the two formulations (differing in lipid composition) had a 10 to 100 times more potent (greater ability to reduce CFU levels) than free amikacin or free tobramycin. A daily human dose of 600 mg TOBI® (a tobramycin inhalation solution made by the Chiron Corporation, Ameryville, Calif.), or about 375 mg/m$^2$, corresponds to a daily rat dose of 9.4 mg. Thus the data can be directly correlated to a 10 to 100 fold improvement in human efficacy. It should be noted that a two-log reduction is the best that can be observed in this model. A 100-fold reduction in *P. aeruginosa* in sputum assays has been correlated with improved pulmonary function (Ramsey et al., 1993). The sustained release of the liposomal amikacin formulations indicate that a lower dose and/or less frequent dosing can be employed to obtain a greater reduction in bacterial growth than can be obtained with free aminoglycoside.

The efficacy of liposomal amikacin formulation was studied in a model for chronic pulmonary infection where *P. aeruginosa* was embedded in an agarose bead matrix that was instilled via the trachea of Sprague/Dawley rats. Three days later free amikacin or liposomal amikacin was dosed every day (FIG. 3) or every other day (FIG. 4) at 1 mg/rat or 10 mg/rat of the given aminoglycoside or 1 mg/rat liposomal amikacin, as well as with blank liposomes (lipid vehicle) as the control, with five rats per group.

The homogenized rat lungs (frozen) following the 14 day experiment were analyzed for aminoglycoside content and activity. The clinical chemical assay was performed using a TDX instrument while the bioassay was performed by measuring inhibition zones on agar plates embedded with *Bacillus subtilis*. The results are shown in Table 9:

TABLE 9

Results from liposomal amikacin formulation treated rat lungs infected with *P. aeruginosa*.

| Formulation | Bioassay (microgram/mL) | Clinical Assay (microgram/mL) |
|---|---|---|
| Lip-An-14 (1 mg/rat) | 9.5 | 9.1 |
| Lip-An-15 (1 mg/rat) | 21.5 | 18.4 |
| Free amikacin (10 mg/rat) | nd | 2.0 |
| Free tobramycin (10 mg/rat) | nd | 1.4 |

Drug weights are for the drug normalized to the absence of any salt form.

The Table 10 results indicate that aminoglycoside is present and active for both liposomal antiinfective formulations, while little can be detected for the free aminoglycoside even at the 10-fold higher dose. These further results establish the sustained release characteristics of liposomal antiinfective formulations, and also confirm that that antiinfective which remains is still active. Of the above formulations only the free tobramycin (0.1 microgram/mL) exhibited any detectable levels of aminoglycoside in the kidneys.

Figure 5:
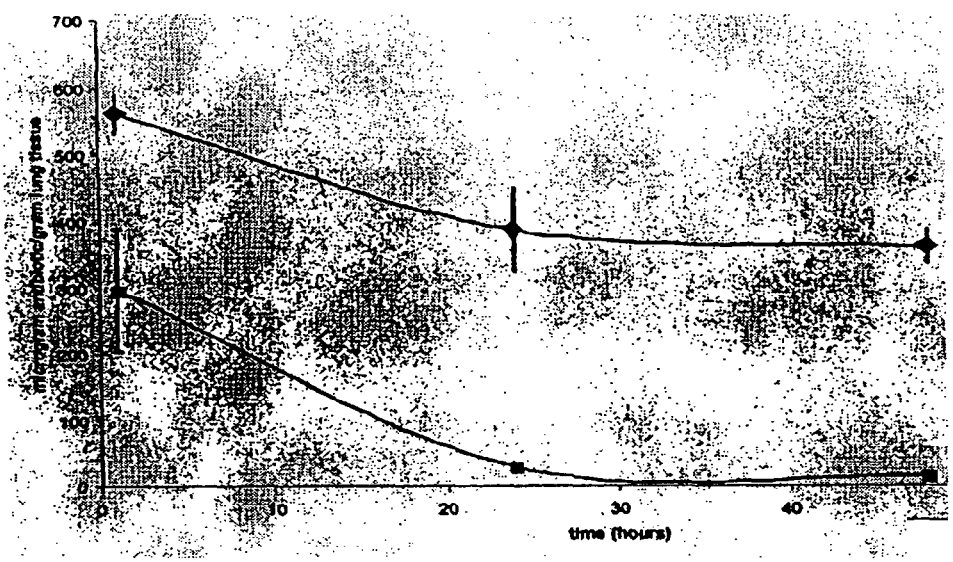
FIG. 5 depicts a graphical representation of sustained release for liposomal/complexed amikacin and tobramycin.
Figure 6:
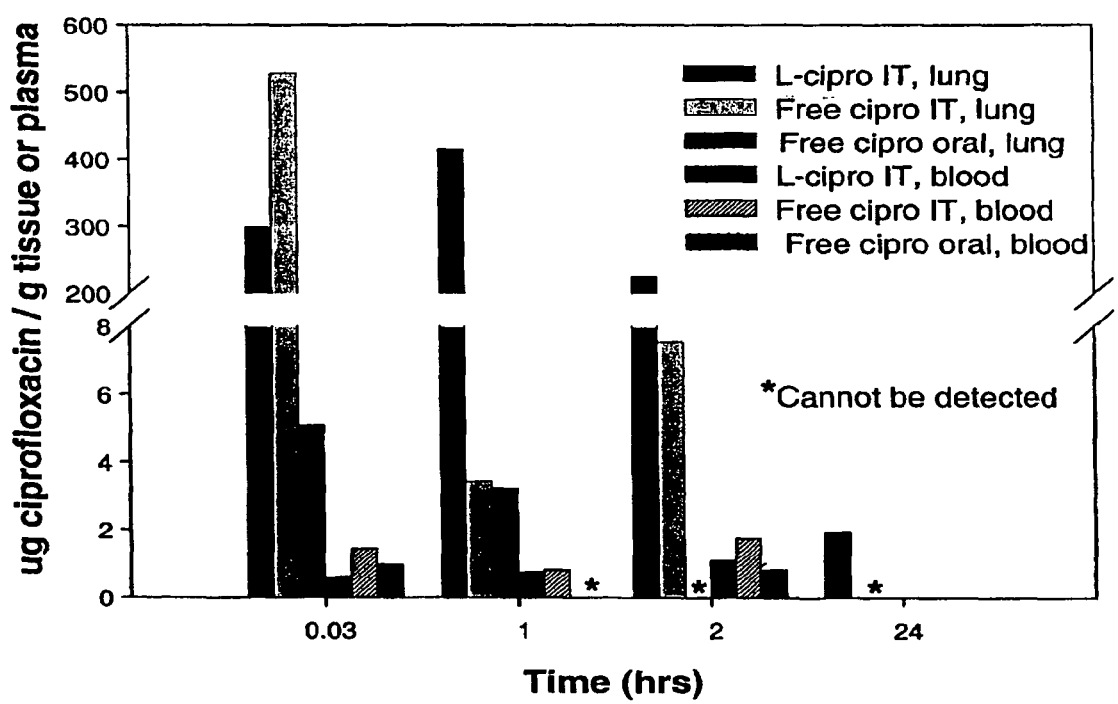
FIG. 6 depicts data on free or complexed ciprofloxacin.

The sustained release and depot effect of liposomal amikacin formulation is further demonstrated in FIG. 5. Rats were given a chronic pulmonary infection where *P. aeruginosa* was embedded in an agarose bead matrix that was instilled via the trachea, using the same beads employed in the efficacy studies. The rats were then given free tobramycin or liposomal amikacin (formulation Lip-An-14) via intratracheal administration at the same dose (2 mg/rat). The data, measured in microgram antiinfective per gram lung tissue over time, show that liposomal antiinfective exhibits a sustained release and depot effect while free tobramycin revealed negligible levels in the lungs by 24 hours, primarily due it is believed to rapid systemic absorption. This greater than a hundred-fold increase of antiinfective in the lung for liposomal amikacin formulations in an infected rat supports the idea of a sustained release liposomal antiinfective that can be taken significantly less often than the currently approved TOBI® formulation (a tobramycin inhalation solution made by the Chiron Corporation, Ameryville, Calif.).

The pharmacokinetics of amikacin was determined in rats following intratracheal (IT) administration of either free tobramycin or liposomal amikacin. A dose of 2 mg/rat was administered. The depot effect of liposomal antiinfective technology is demonstrated in that in comparison to free tobramycin given IT, a greater than a hundred-fold increase in drug for liposomal amikacin still remains in the infected lungs twenty-four hours following administration. Thus, the therapeutic level of drug is maintained for a longer period of time in the liposomal formulations compared to free tobramycin.

Figure 7:
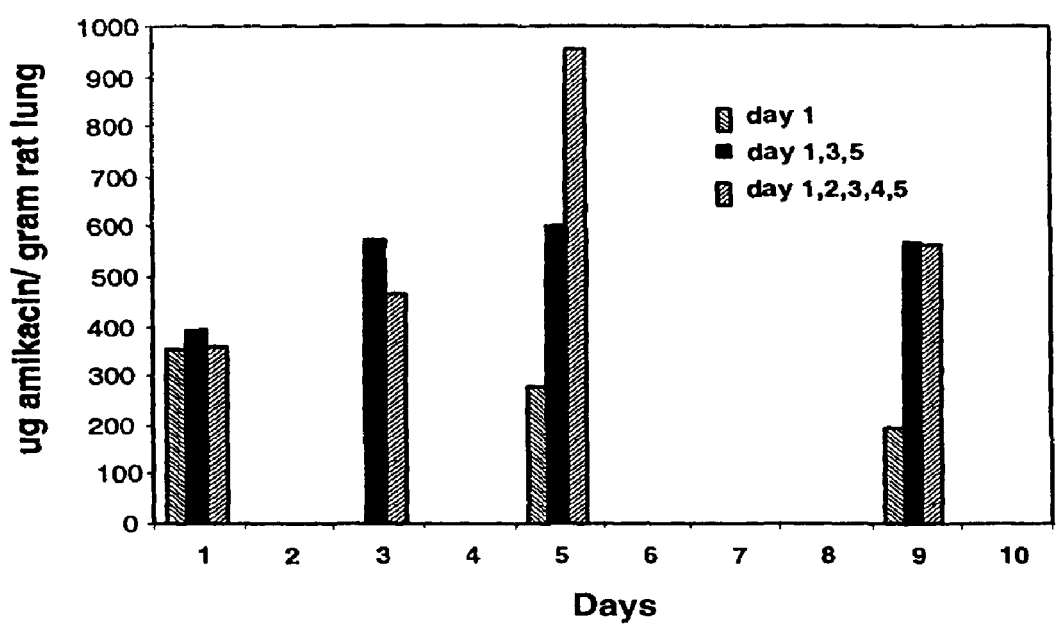
FIG. 7 depicts a graphical representation of drug residence in the lung given various dosing schedules.

FIG. 7 shows remarkable residence time and accumulation of effective amounts of antiinfective in the lungs, a result that establishes that relatively infrequent dosings can be used. Each dose is 4 hr. by inhalation (in rat, 3 rats per group, as above) of nebulized liposomal amikacin formulations (DPPC/Chol., 1:1) at 15 mg/mL amikacin. Dosing was at either day one; day one, three and five; or day one, two, three, four and five. Rats providing a given data bar were sacrificed after the respective dosing of the data bar. The formulation is made as in the Example.

Similar anti-infectives can be utilized for the treatment of intracellular infections like pulmonary anthrax and tularemia. In pulmonary anthrax the anthrax spores reach the alveoli in an aerosol. The inhaled spores are ingested by pulmonary macrophages in the alveoli and carried to the regional tracheobronchial lymph nodes or mediastinal lymph nodes via the lymphatics (Pile et al., 1998; Gleiser et al., 1968). The macrophage is central in the both the infective pathway and is the major contributor of host self-destruction in systemic (inhalation) anthrax. In addition to its attributes of sustained release and targeting, liposomal antiinfective formulation technology can enhance cellular uptake and can use alveolar macrophages and lung epithelial cells in drug targeting and delivery. The possession of these characteristics is believed to facilitate the treatment of these intracellular infections, which infections occur in the lungs and are transported by macrophages. More importantly, these characteristics should make the antiinfective more effective in that the liposomal antiinfective should be phagocytized by the very cells containing the disease. The antiinfective would be released intracellularly in a targeted manner, thereby attacking the infection before it is disseminated. The encapsulated drug can be an already approved pharmaceutical like ciprofloxacin, tetracycline, erthyromycin or amikacin. Liposomal ciprofloxacin formulations have been developed.

In a study, this compound was administered to mice and compared to both free ciprofloxacin administered intratracheally and free ciprofloxacin administered orally, with all three compounds given at the same dose (FIG. 6). The dose for each mouse was 15 mg/kg, with three mice per group. Liposomal ciprofloxacin was in DPPC/Cholesterol (9:1), at 3 mg/mL ciprofloxacin, with the formulation produced as in the Example. The lipid to drug ratio was 12.5:1 by weight. In comparison to orally administered ciprofloxacin, liposomal ciprofloxacin was present in the mice lungs at amounts over two orders of magnitude higher than free ciprofloxacin. Moreover, only liposomal ciprofloxacin showed levels of drug in the lung after 24 hours, while the orally administered drug was undetectable in less than two hours. This data supports the use of liposomal ciprofloxacin formulations and other antiinfectives like aminoglycosides, tetracyclines and macrolides for the treatment and for the prophylactic prevention of intracellular diseases used by bioterrorists.

8.3. Liposome Parameters

The lipids to be employed are dissolved in ethanol to form a lipid-ethanol solution. The lipid-ethanol solution is infused in an aqueous or ethanolic solution containing the molecule of the bioactive agent to be entrapped. The lipids spontaneously form vesicles.

Table 10 discloses liposomal antiinfective formulation parameters where the lipids are DPPC and cholesterol.

TABLE 10

| Additional liposomal antiinfective formulation parameters. Amikacin Liposomes (DPPC/Chol) | | | | | |
|---|---|---|---|---|---|
| Batch # | [Total Amikacin] mg/mL | [Total Lipid]* mg/mL | % of Total Amikacin that is Entrapped | L/D (w/w)** | Liposome Mean Diameter (μm) |
| 1 | 14.7 | 44.8 | 96.7 | 3.2 | — |
| 2 | 21.4 | 71.3 | 98.1 | 3.4 | 0.36 |
| 3 | 18.5 | 46.6 | 90.2 | 2.8 | 0.27 |
| 4 | 9.4 | 40.6 | 95.0 | 4.5 | 0.34 |
| 5 | 15.8 | 52.3 | 97.7 | 3.4 | 0.27 |
| 6 | 20.7 | 31.8 | 95.5 | 1.6 | 0.25 |
| 7 | 20.6 | 40.0 | 98.6 | 2.0 | 0.25 |

TABLE 10-continued Additional liposomal antiinfective formulation parameters.
Amikacin Liposomes (DPPC/Chol)

| Batch # | [Total Amikacin] mg/mL | [Total Lipid]* mg/mL | % of Total Amikacin that is Entrapped | L/D (w/w)** | Liposome Mean Diameter (μm) |
|---|---|---|---|---|---|
| 8 | 19.9 | 40.7 | 98.3 | 2.1 | 0.28 |
| 9 | 20.9 | 40.5 | 98.1 | 2.0 | 0.28 |

*DPPC/Cholesterol liposomes where the DPPC/Chol mole ratio is approximately 1:1.
**Only the entrapped amount of amikacin was considered in calculating L/D.

Further information on forming liposomal antiinfective formulations can be found in PCT/US03/06847, filed Mar. 5, 2003, which is incorporated herein by reference in its entirety.

Entrapped volume is a basic characteristic of a liposomal formulation and is determined as the volume of intraliposomal aqueous phase per unit of lipid. It is generally expressed in the units of μliters/μmole. One often assumes that when liposomes are formed the concentration of the solute inside liposomes is equal to that outside in the bulk solution. A higher entrapped volume then would lead to higher drug/lipid ratio, i.e., a higher overall drug concentration for the final formulation.

In formulating liposomal amikacin, however, it has been found that the actual drug/lipid ratio that can be produced was more than 3-fold higher that one would expect based on the entrapped volume. Table 11 shows the results for 4 different sample preparations of lipid antiinfective formulations (see Example 2 in the Exemplification section).

TABLE 11

Amikacin loading into liposomes prepared by different methods.

| Measured Parameter | Sample # | | | |
|---|---|---|---|---|
| | 1 | 2 | 3 | 4 |
| Lipids concentration (mg/mL) | 35.1 | 39.5 | 50.4 | 45.0 |
| AMK concentration (mg/mL) | 19.9 | 20.7 | 10.5 | 5.0 |
| Actual Lipid/Drug (w/w) | 1.8 | 1.9 | 4.8 | 9.0 |
| Entrapped volume (ul/umole) | 2.4 | 2.5 | 2.9 | 1.6 |
| Expected Lipid/Drug (w/w) | 5.6 | 6.0 | 4.1 | 8.1 |
| Expected/Actual L/D ratio | 3.19 | 3.17 | 0.85 | 0.90 |
| Liposome Size (um) | 0.230 | 0.217 | 4.65 | 3.96 |

Samples 1 and 2 were made by the ethanol infusion procedure disclosed herein, and Samples 3 and 4 were made by liposome formation techniques known in the art.

Concentrations of amikacin were measured by immunofluorescent assay using INNOFLUO Seradyn reagent set on TDx analyzer. Lipids were measured by reverse-phase HPLC using C-8 column and Light scattering detector.

Liposomal volume (volume occupied by liposomes per unit of total volume) in samples #1-3 was determined by measuring the concentration of the fluorescent probe (Sulforhodamine 101 or Carboxyfluorescein) in the total volume and in the filtrate volume of the formulation obtained by centrifugation in CentriSart filtering device. Probe concentration in the filtrate is higher that the average one due to exclusion of the probe from the volume occupied by liposomes.

In sample #4, liposomal volume was determined by measuring the concentration of Potassium ion in a sample after adding fixed amount of it, 250 ul of KCl ($V_{add}$) into 10 mL liposomal suspension ($V_o$). Samples were then centrifuged 30 min at 4000 rpm and a supernatant was taken to measure potassium ion (K) by Cole-Parmer potassium-sensitive electrode. Potassium concentration measured was always higher than expected due to exclusion of potassium ions from the volume occupied by liposomes. In the control, an equal amount of KCl was added into 10 mL saline solution. Potassium concentration in control $K_c$ was measured. Aqueous and liposomal volumes were than estimated as:

$$v_a = \frac{K_c}{K}(V_o + V_{add}) - V_{add}, \quad v_L = 1 - v_a.$$

Knowing the liposomal volume and the lipid concentration one can determine the entrapped volume:

$$v_{ent} = \frac{v_L - L_w}{L_m},$$

where $L_w$ and $L_m$ are the weight and molar lipid concentrations, respectively. Lipid density is assumed to be close to 1 mg/mL. Consequently, one can estimate expected Lipid/Drug ratio that the sample would have if the drug was distributed ideally in the aqueous spaces inside and outside liposomes:

$$\left(\frac{L}{D}\right)_{ex} = \frac{L_w}{D_o(v_L - L_w)} = \frac{M_L}{D_o v_{ent}},$$

where $D_o$ is the bulk concentration of the drug during liposome formation, $M_L$ is the average molecular weight of lipids.

As one can see, actual L/D ratios for samples #1 and #2 (1.8 and 1.9) are consistently lower than one would expect from even distribution of amikacin (5.6 and 6.0), while L/D's for samples #3 and #4 are closer to theoretical values.

A similar comparison was made between 2 sample preparations of a lipid antiinfective formulations where gentamicin sulfate was the antiinfective (see Example 3 in the Exemplification section). The data in Table 12 indicate that the method disclosed herein provides unexpectedly high entrapment of gentamicin. In both samples #5 and #6, the actual Lipid/Drug ratios were almost twice the theoretically expected value.

TABLE 12

Gentamicin loading into liposomes prepared by different methods.

| Measured Parameter | Sample # | |
|---|---|---|
| | 5 | 6 |
| Lipids concentration (mg/mL) | 44.8 | 41.8 |
| Drug concentration (mg/mL) | 14.2 | 14.9 |
| Actual Lipid/Drug (w/w) | 3.2 | 2.8 |
| Entrapped volume (ul/umole) | 2.3 | 2.7 |
| Expected Lipid/Drug (w/w) | 5.7 | 5.4 |
| Expected/Actual L/D ratio | 1.82 | 1.92 |
| Liposome Size (um) | 0.226 | 0.236 |

8.4. Drug Release Mediated by *P. Aeruginosa* Infection

Release of drug in an active form in the vicinity of the infections is an important aspect of the action of liposomal drug formulation of the present invention. The potential for such targeted release was tested by monitoring the release of drug upon incubation with sputum from a CF patient, release in the lungs of rats pre-inoculated with *P. aeruginosa*, as well as the activity of against cultures of *P. aeruginosa*.

The release of amikacin by direct incubation of a culture of *P. aeruginosa* with a liposomal amikacin formulation of the present invention was previously discussed. To further investigate this phenomenon, a liposomal amikacin formulation was incubated with a preparation of sputum from a cystic fibrosis patient with *P. aeruginosa* infection. Expectorated sputum was liquefied with bovine DNase I and alginate lyase for 2 hr. at 37° C. A liposomal amikacin formulation or soluble amikacin (1 mg/mL amikacin) was mixed 1:1: with liquefied sputum or control and incubated at 37° C. with gentle shaking. Aliquots were analyzed for amikacin concentration by Abbott TDx Analyzer. Intact liposomes were lysed in a separate aliquot of each sample using a detergent, 1% Triton X-100. Supernatants from each sample were used for analysis. Over the period of 48 hours, (80-90%) of the amikacin was released in a time-dependent manner from the lipid composition under these conditions, indicating that drug release may occur at the sites of infection in the CF lung.

Release of free drug from liposomes in vivo was compared for rats that had been instilled with agar beads containing *P. aeruginosa* ($3.5 \times 10^4$ CFU/rat) versus those that had not. Three days after bead instillation, rats were allowed to inhale liposomal amikacin formulations of the present invention (approx. 6 mg/kg daily dose) every day (no bacteria group) or every other day for 14 days (group instilled with beads). 24 hours after the last treatment, the total amikacin and free amikacin were measured as described above. In rats that had received bacteria, an average of approximately 50-70% of the detected amikacin was in the free form, i.e. released from the liposome. In the rats that had not received bacteria approximately 20-25% of the drug was in free form. These data strongly suggest that release of free amikacin from the liposome may be mediated by the presence of *P. aeruginosa* in vivo.

An in vitro test of release and activity was performed under conditions similar to the pharmacokinetics in the lung, where it has been previously shown that free antibiotic is cleared on the time scale of a few hours. Free amikacin or a liposomal amikacin formulation was incubated with *P. aeruginosa* PA01 ($\sim 10^8$/mL) in sterile 0.5 mL Slide-A-Lyzer cartridges at varying drug concentrations. Free drug dialyzes out of the cartridges on the time scale of hours under these conditions. After 24 hrs., the samples were withdrawn from the cartridges and plated to measure CFU. In the preliminary experiments free amikacin only slightly reduced the CFU of these samples, while a two log reduction of CFUs was observed for amikacin comprising lipid compositions at the same amikacin concentration (50 μg/mL). These data suggest that amikacin is indeed released in an active form in the presence of bacteria and that the slow release afforded by the formulation makes more effective use of the drug.

The interaction of the liposomal amikacin formulations of the present invention with *P. aeruginosa* or its virulence factors leads to release of amikacin possibly directing release to the site of infection. When amikacin is released it is active against *P. aeruginosa*, and the slow release in the vicinity of the bacteria may have an advantage over the non-specific distribution and rapid clearance of inhaled free drug.

8.5. Effect of Inhaled Liposomal Drug Formulations on the Function of Alveolar Macrophages The liposomal amikacin formulations of the present invention are in one embodiment a nanoscale (200-300 nm) liposome-encapsulated form of amikacin that is formulated to treat chronic *P. aeruginosa* infections in cystic fibrosis patients. It is designed for inhalation with sustained release of amikacin in the lung. Because alveolar macrophages are known to avidly take up particles in this size range, the effect of the liposomal formulations on these cells is of particular interest. The basal and stimulated functions of rat alveolar macrophages obtained by lavage were studied with and without administration of liposomal amikacin formulations and compared to various controls.

Aerosols of the liposomal amikacin formulations, amikacin, placebo liposomes and saline were generated with a PARI LC Star nebulizer and inhaled by CD®IGS female rats in a nose-only inhalation chamber. Inhalation therapy was conducted for 4 hr for 14 consecutive days, such that the estimated daily lung dose of total lipid was approximately 12 mg/kg for the liposomal amikacin group and 11 mg/kg for the placebo liposome group. Half the rats were euthanized on day 15. The remaining rats were euthanized on day 43. Bronchial alveolar lavage fluid (BALF) was collected from each rat and stored at −80° C. for subsequent assay of nitric oxide (as represented by total nitrates) and tumor necrosis factor alpha (TNF-α). The cells from the BALF were collected by centrifugation, counted and cultured in medium with and without lipopolysaccharide (LPS) for 24 hr. The supernatants from these cultures were collected by centrifugation and assayed for nitric oxide and TNF-α. The phagocytic function of BAL macrophages (($10^6$)/mL) was tested by measuring the overnight uptake of opsonized fluorescent microspheres (0.2 μm, 2 ($10^9$)/mL).

Inhalation of the liposomal amikacin formulation, empty liposomes, soluble amikacin, or saline for 14 consecutive days did not produce a significant acute or delayed inflammatory response in the lungs of rats as evident by levels of nitric oxide (nitrates) and TNF-α in BALF which were insignificantly different from controls, although there was an early trend toward higher NO levels in all groups receiving inhalants, including controls. The total recovery of cells was insignificantly different in all groups with an early trend toward more polymorphonuclear leukocytes in all groups receiving inhalants. Rat alveolar macrophages had normal functions after exposure to the aerosols of the above test articles despite the fact that they appeared enlarged on day 15 in groups inhaling liposomes. The concentrations of nitrates and TNF-α detected upon culturing of alveolar macrophages in medium on day 15 or 43 of the study were insignificantly different from controls. The macrophages responded normally when stimulated by LPS, producing substantial concentrations of nitric oxide (20-40 nmol/$10^6$ cells) and TNF-α (5-20 ng/$10^6$ cells). These macrophages also had normal phagocytic functions, as shown by identical uptake of fluorescent beads compared to untreated controls.

Inhalation of the liposomal amikacin formulations for 14 consecutive days did not substantially affect the function of alveolar macrophages in terms of phagocytosis of opsonized beads, production of inflammatory mediators TNF and NO.

9. Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 50 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions (e.g., the antiinfective) because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

10. Formulation

The lipid antiinfective formulations of the present invention may comprise an aqueous dispersion of liposomes. The formulation may contain lipid excipients to form the liposomes, and salts/buffers to provide the appropriate osmolarity and pH. The formulation may comprise a pharmaceutical excipient. The pharmaceutical excipient may be a liquid, diluent, solvent or encapsulating material, involved in carrying or transporting any subject composition or component thereof from one organ, or portion of the body, to another organ, or portion of the body. Each excipient must be "acceptable" in the sense of being compatible with the subject composition and its components and not injurious to the patient. Suitable excipients include trehalose, raffinose, mannitol, sucrose, leucine, trileucine, and calcium chloride. Examples of other suitable excipients include (1) sugars, such as lactose, and glucose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

EXEMPLIFICATION

Example 1

The following is a detailed description of the manufacture of 150 mL of Liposomal/complexed amikacin.
Total Intial Volume=1.5 L
Ethanol Content=23.5% (v/v)
Lipid Composition: DPPC/Chol (1:1 mole ratio)
Intial [Lipid]=7.6 mg/mL
Intial [amikacin sulfate]=57.3 mg/mL
Final product Volume=150 mL I) Compounding and Infusion:

7.47 g DPPC and 3.93 g Cholesterol were dissolved directly in 352.5 mL ethanol in a 50 C water bath. 85.95 g amikacin sulfate was dissolved directly in 1147.5 mL PBS buffer. The solution is then titrated with 1ON NaOH or KOH to bring the pH to approximately 6.8.

352.5 mL ethanol/lipid was added or infused to the 1147.5 mL amikacin/buffer to give a total intial volume of 1.5 L. The ethanol/lipid was pumped @-30 mUmin (also called infusion rate) with a peristaltic pump into the amikacin/buffer solution which was being rapidly stirred at 150 RPM in a reaction vessel on a stir plate at room temperature The product was stirred at room temperature for 20-30 minutes.

II) Diafiltration or "Washing" Step:

The mixing vessel was hooked up to a peristaltic pump and diafiltration cartridge. The diafiltration cartridge is a hollow membrane fiber with a molecular weight cut-off of 500 kilodaltons. The product was pumped from the reaction vessel through the diafiltration cartridge and then back into the mixing vessel at room temperature. A back pressure of approximately 7 psi is created throughout the cartridge. Free amikacin and ethanol was forced through the hollow fiber membrane by the back pressure leaving the liposomal amikacin (product) behind. The product was washed 8 times at room temperature. Fresh PBS buffer was added (via another peristaltic pump) to the reaction vessel to compensate for the permeate removal and to keep a constant product volume.

The product was concentrated.

Example 2

High Liposomal Entrapment of Amikacin.

Four samples of lipid antiinfective formulations were prepared at various lipid and antiinfective concentrations according to the following procedures.

Sample #1. Amikacin sulfate 1.72 kg was dissolved in 23 Liters saline solution (0.9% NaCl) and pH was adjusted to 6.5 by adding necessary amount NaOH. Lipids—98.2 g DPPC and 51.8 g Cholesterol were dissolved in 7 liters ethanol. Liposomes were formed by infusion of lipid solution into amikacin solution at a rate of ~600 mL/min and under constant stirring. Resulting suspension was then washed to remove ethanol and un-entrapped amikacin by diafiltration using an Amersham Hollow Fiber cartridge 500 kD pore size. The suspension was concentrated to a final volume of ~3.5 L.

Sample #2. The procedure was similar to that for sample #1 with all material quantities scaled down 100 fold. Amikacin sulfate 17.2 g was dissolved in 230 mL saline solution (0.9% NaCl) and pH was adjusted to 6.6 by adding necessary amount NaOH. Lipids-0.982 g DPPC and 0.518 g Cholesterol were dissolved in 70 mL ethanol. Liposomes were formed by infusion of the lipid solution into the amikacin solution at a rate of ~300 mL/min and under constant stirring. The resulting suspension was then washed to remove ethanol and un-entrapped amikacin by diafiltration using an Amersham Hollow Fiber cartridge. The suspension was concentrated to a final volume of ~35 mL.

Sample #3. Liposomes were made by a procedure known as SPLV. Amikacin sulfate 1.4 g was dissolved in 20 mL saline solution (0.9% NaCl) making pH 3.3. Lipids, 0.666 g DPPC and 0.333 g Cholesterol were dissolved in 40 mL dichloromethane. Amikacin and lipid solutions were mixed together in a 500 mL round flask and briefly sonicated to form an emulsion. Flask was then connected to a BUCHI Rotavapor system to remove dichloromethane at low vacuum (−5 inches Hg) and temperature 50° C. and constant rotation until the amikacin-lipid mixture formed a gel. When the gel eventually collapsed, vacuum was gradually increased to −20 inches Hg and drying continued for 30 more minutes. The final volume of formed liposomal suspension was 22 mL.

Sample #4. The procedure was similar to that for sample #3. Amikacin sulfate 1.3 g was dissolved in 20 mL of saline solution, and pH was adjusted to 6.5 by adding NaOH. Lipids, 0.583 g DPPC and 0.291 g Cholesterol were dissolved in 35 mL dichloromethane. The sonication step was skipped. The solvent removal step on the Rotavapor system was carried out at 40° C. for 2 hr. Final volume was 20 mL.

Example 3

High Liposomal Entrapment of Gentamicin.

Sample #5. Gentamicin sulfate 20.0 g was dissolved in 230 mL saline solution (0.9% NaCl) and pH was adjusted to 6.5 by adding necessary amount of sulfuric acid. Lipids—0.982 g DPPC and 0.518 g Cholesterol were dissolved in 70 mL ethanol. Liposomes were formed by infusion of lipid solution into gentamicin solution at a rate of ~500 m/min and under constant stirring. Un-entrapped gentamicin and ethanol were removed by diafiltration using an Amersham Hollow Fiber cartridge. The suspension was concentrated to a final volume of ~35 mL.

Sample #6. The procedure was similar to that for sample #5, except: Gentamicin sulfate 17.0 g was dissolved in 230 mL $Na_2SO_4$ 100 mM solution and pH was adjusted to 6.5 by adding necessary amount of $H_2SO_4$. Lipids—0.982 g DPPC and 0.518 g Cholesterol were dissolved in 75 mL ethanol.

Example 4

Entrapment of Other Salt Forms of Amikacin.

Sample #7. The procedure was similar to that for sample #2 under Example 2. Amikacin base 10.7 g and Citric acid 4.2 g were dissolved in 230 mL saline solution (0.9% NaCl). pH of resulted amikacin-citrate solution was 6.2. Lipids—0.982 g DPPC and 0.518 g Cholesterol were dissolved in 70 mL ethanol. Liposomes were formed by infusion of lipid solution into amikacin solution at a rate of ~500 mL/min and under constant stirring. Un-entrapped amikacin and ethanol were removed by diafiltration using an Amersham Hollow Fiber cartridge. The suspension was concentrated to a final volume of ~35 mL.

The actual Lipid/Drug ratio was similar to that for sample #2 and again lower than expected (Drug entrapment higher than expected). Considering the fact that the entrapped volume in the sample #7 was only 1.5 (compared to 2.5 for sample #2), the Expected/Actual L/D ratio was as high as 5.2. Thus, liposomal amikacin citrate, like amikacin sulfate, can also be formulated with high entrapment.

TABLE 13

Samples 5-7 parameter summary.

| Measured Parameter | Sample # | | |
|---|---|---|---|
| | 5 | 6 | 7 |
| Lipids concentration (mg/mL) | 44.8 | 41.8 | 41.7 |
| Drug concentration (mg/mL) | 14.2 | 14.9 | 17.8 |
| Actual Lipid/Drug (w/w) | 3.2 | 2.8 | 2.3 |
| Entrapped volume (ul/umole) | 2.3 | 2.7 | 1.5 |
| Expected Lipid/Drug (w/w) | 5.7 | 5.4 | 12.2 |
| Expected/Actual L/D ratio | 1.82 | 1.92 | 5.20 |
| Liposome Size (um) | 0.226 | 0.236 | 0.234 |

Example 5

Bioavailability of Amikacin from Inhaled Liposomal Amikacin Formulations in the Rat.

The rate of release of amikacin from the liposomes was measured after inhalation by rats and compared to inhaled soluble amikacin.

The test items were aerosolized via a Pari LC Star nebulizer attached to a nose-only inhalation chamber. CD®IGS rats received an estimated lung deposited dose of 6 mg/kg of amikacin in the form of a liposomal formulation or 5 mg/kg of soluble amikacin as a single dose or dosed daily for 14 consecutive days. Lung or other tissue was homogenized with a Polytron apparatus. The kinetics of clearance of amikacin from the lung was examined by analysis of lung homogenates at varying time points after the single dose treatment or 1 day and 28 days after administration of the multiple doses. Amikacin levels were measured by immunofluorescence polarization on a Abbott TDx® analyzer in the absence or presence of 1% Triton X-100, which releases amikacin from liposomes. Whole lung samples were spiked with liposomes before homogenization to test the release of amikacin under these conditions. Free and total amikacin were measure with and without 1% Triton X-100 to assess leakage of drug.

Liposomal amikacin, spiked into whole lung samples, showed no significant release of amikacin as a result of tissue homogenization with the Polytron homogenizer in the absence of this detergent. However, addition of 1%Triton X-100 led to recovery of all of the expected drug. Therefore a direct comparison could be made of the total level of amikacin (with detergent) versus the freely available levels in lung tissue.

A high total concentration of amikacin (approx. 500-600 μg/g of lung tissue) was observed immediately after the 6 mg/kg single dose of the liposomal amikacin, which slowly decreased by about 50% over a 7 day period. The temporal profile for the release of free amikacin from these liposomes showed an initial high concentration of free drug, probably resulting from amikacin liberated as a result of nebulization. This phase was followed by a nadir at about 24 hours and a subsequent increase, reaching a maximum of 279 μg/g at 96 hours after administration. By the end of the 7 day experiment, a substantial portion of drug remaining in the lung was in the free form (approximately 50-70%). It appeared that a small portion of the soluble drug administered by inhalation also remained for a long period of time in the lung. However, most of the amikacin administered in soluble form was cleared within several hours, and the apparent free amikacin AUC over 7 days was at least 2× higher for the liposomal amikacin animals than for those that received soluble amikacin. Some aspects of this behavior can be qualitatively modeled with appropriate rate constants for clearance and slow release of drug from liposomes.

After 14 consecutive days of administration (24 hours after the last dose), more than 20% of the total amikacin in the lungs of rats that received liposomal amikacin was present as free drug (approximately 650 μg/g). The total free drug level was even greater than the amount in rats that inhaled soluble amikacin (approx. 500 μg/g).

Free amikacin is released slowly from the liposomes of the liposomal amikacin formulations in the lungs of healthy animals over a time scale of days. The free drug that is released has a relatively long residence time in the lung as seen by a substantial depot of free drug in the lungs.

Example 6

In-Line Infusion Process

The essence of the In-Line infusion process is that a stream of lipid solution is mixed with a stream of antiinfective solution "in-line" via, for example, a Y-connector which connects to a length of tubing, termed a mixing tube, where further mixing can occur. In this regard, this new process differs from the 'conventional' ethanol infusion process, where lipid solution is infused as a stream into a bulk of amikacin solution.

Amikacin and Lipid Solutions Preparation.

Amikacin sulfate 12.0 g was dissolved in 200 mL water and pH was adjusted to 6.5 by adding necessary amounts of 25% NaOH solution. Lipids, 1.480 g DPPC and 0.520 g cholesterol, were dissolved in a mixture of 60 mL ethanol and 10 mL water. These amounts result in a 300 mL batch after infusion at a lipid/amikacin flow rate of 300/500 mL/min, respectively. Volumes can be proportionally adjusted for larger scale or if different flow rates are desired.

The amikacin solution prepared according to above results in approximately 40 mg/mL amikacin (per base) solution. The lipid solution as presented was DPPC/Chol (mole ratio of 60/40) with a total lipid of approximately 20 mg/mL solution (90% ethanol). Lipids were heated to ~40° C. for faster dissolution.

The exact amounts needed for a 300 mL batch are: amikacin 150 mL, lipid 90 mL, and 60 mL of additional saline (or water) which is added after or during infusion to adjust final ethanol concentration.

Manufacturing Procedure.

One embodiment of the infusion system is shown in FIG. 8.

Lipid and Amikacin solutions are mixed in-line using a Y-connector (ID 3.2 mm, OD 6.4 mm) at flow rates ~300/500 mL/min (i.e. ~1/1.67 volume ratio instead of ~1/3.35 in the conventional process). A MasterFlex tube L/S 25 (ID 4.8 mm) was used to deliver the lipid solution and a L/S 17 tube (ID 6.4 mm) was used to deliver the amikacin solution. To obtain synchronous flow rates, two pump heads with one MasterFlex drive were used. According to the tube cross-section areas, the theoretical flow rate ratio should be $4.8^2/6.4^2=0.562=1/1.78$. When the pump drive was set to 500 mL/min for Amikacin tube L/S 17, the measured flow rates were ~300/500=1/1.67.

Since the lipid solution contains 90% ethanol, the in-line mixture had ~34% ethanol. To prevent amikacin precipitation, NaCl solution can be added after or during infusion at a flow rate 100-200 mL/min (it is assumed that the liposomes are already formed at this point). Thus the final mixture would have ~27% ethanol, of which all free amikacin is expected to be soluble.

Total liquid infusion flow rate, 800-1000 mL/min, is comparable to the permeate flow rate when using two big diafiltration cartridges. This makes it possible to do simultaneous infusion and concentration by diafiltration.

The resulting liposome suspension was washed to remove free amikacin by diafiltration using an Amersham hollow fiber cartridge UFP-500-C-3MA (membrane area 140 cm$^2$, fiber ID 0.5 mm). In the first step, the suspension was concentrated to nearly half of the original volume (150 mL). Then, during diafiltration to wash, the suspension was re-circulated and fresh saline solution was fed into the mixture at a rate of ~6 mL/min in order to match the permeate rate and thus maintain a constant volume. Diafiltration continued until 4 times the suspension volume of the feeding saline solution was dispensed (i.e., 4*150 mL=600 mL). This diafiltration/washing procedure will be referred to as 4 "washes". Finally, the suspension was concentrated (diafiltration without saline input) to obtain the Final Product at a desired amikacin and lipid concentration. The recirculation flow rate during the diafiltration step was ~350 mL/min, and during the final concentration step it was gradually reduced to ~150 mL/min in order to maintain the inlet pressure below 10 PSI.

References

1. Veldhuizen, R., Nag, K., Orgeig, S. and Possmayer, F., The Role of Lipids in Pulmonary Surfactant, Biochim. Biophys. Acta 1408:90-108 (1998).
2. Hagwood, S., Derrick, M. and Poulain, F., Structure and Properties of Surfactant Protein B, Biochim. Biophys. Acta 1408:150-160 (1998).
3. Johansson, J., Structure and Properties of Surfactant ProteinC, Biochim. Biophys. Acta 1408:161-172 (1998).
4. Ikegami, M. and Jobe, A. H., Surfactant Protein Metabolism in vivo, Biochim. Biophys. Acta 1408:218-225 (1998).

5. Couveur, P., Fattel, E. and Andremont, A., Liposomes and Nanoparticles in the Treatment of Intracellular Bacterial Infections, Pharm. Res. 8:1079-1085 (1991).
6. Gonzales-Rothi, R. J., Casace, J., Straub, L., and Schreier, H., Liposomes and Pulmonary Alveolar Macrophages: Functional and Morphologic Interactions, Exp. Lung Res. 17:685-705 (1991).
7. Swenson, C. E., Pilkiewicz, F. G., and Cynamon, M. H., Liposomal Aminoglycosides and TLC-65 Aids Patient Care 290-296 (December, 1991).
8. Costerton, J. W., Stewart, P. S., and Greenberg, E. P., Bacterial Biofilms: A Common Cause of Persistent Infections, Science 284:1318-1322 (1999).
9. Cash, H. A., Woods, D. E., McCullough, W. G., Johanson, J. R., and Bass, J. A., A Rat Model of Chronic Respiratory Infection with *Pseudomonas aeruginosa*, American Review of Respiratory Disease 119:453-459 (1979).
10. Cantin, A.M. and Woods, D. E. Aerosolized Prolastin Suppresses Bacterial Proliferation in a Model of Chronic *Pseudomonas aeruginosa* Lung Infection, Am. J. Respir. Crit. Care Med. 160:1130-1135 (1999).
11. Ramsey, B. W., Dorkin, H. L., Eisenberg, J. D., Gibson, R. L., Harwood, I. R., Kravitz, R. M., Efficacy of Aerosolized Tobramycin in Patients with cystic Fibrosis. New England J. of Med. 328:1740-1746 (1993).
12. Mendelman, P. M., Smith, A. L., Levy, J., Weber, A., Ramsey, B., Davis, R. L., Aminoglycoside Penetration, Inactivation, and Efficacy in Cystic Fibrosis Sputum, American Review of Respiratory Disease 132:761-765 (1985).
13. Price, K. E., DeFuria, M. D., Pursiano, T. A. Amikacin, an aminoglycoside with marked activity against antibiotic-resistant clinical isolates. J Infect Dis 134:S249261(1976).
14. Damaso, D., Moreno-Lopez, M., Martinez-Beltran, J., Garcia-Iglesias, M. C. Susceptibility of current clinical isolates of *Pseudomonas aeruginosa* and enteric gram-negative bacilli to Amikacin and other aminoglycoside antibiotics. J Infect Dis 134:S394-90 (1976).
15. Pile, J. C., Malone, J. D., Eitzen, E. M., Friedlander, A. M., Anthrax as a potential biological warfare agent. Arch. Intern. Med. 158:429-434 (1998).
16. Gleiser, C. A., Berdjis, C. C., Hartman, H. A., & Glouchenour, W. S., Pathology of experimental respiratory anthrax in Macaca mulatta. Brit. J. Exp. Path., 44:416-426 (1968).

Incorporation by Reference

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

Equivalents

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A liposomal aminoglycoside formulation comprising a liposome having a lipid bilayer and an aminoglycoside encapsulated therein, wherein the amount of the lipid by weight is less than or equal to the amount of the aminoglycoside by weight, the lipid bilayer comprises a neutral phospholipid and a sterol, and the liposome has a mean diameter of 0.1 to 0.5 microns.
2. The liposomal aminoglycoside formulation of claim 1, wherein the amount of the lipid is less than or equal to 75% of the amount of the aminoglycoside by weight.
3. The liposomal aminoglycoside formulation of claim 1, wherein the amount of the lipid is less than or equal to 50% of the amount of the aminoglycoside by weight.
4. The liposomal aminoglycoside formulation of claim 1, wherein the aminoglycoside is selected from the group consisting of amikacin, gentamicin, and tobramycin.
5. The liposomal aminoglycoside formulation of claim 1, wherein the aminoglycoside is amikacin.
6. The liposomal aminoglycoside of claim 1, wherein the aminoglycoside is gentamicin.
7. The liposomal aminoglycoside formulation of claim 1, wherein the aminoglycoside is tobramycin.
8. The liposomal aminoglycoside of claim 1, wherein the neutral phospholipid is dipalmitoylphosphatidylcholine (DPPC).
9. The liposomal aminoglycoside formulation of claim 1, wherein the sterol is cholesterol.
10. The liposomal aminoglycoside formulation of claim 1, wherein the neutral phospholipid is DPPC, and the sterol is cholesterol.
11. The liposomal aminoglycoside formulation of claim 1, wherein the aminoglycoside is amikacin, the neutral phospholipid is DPPC and the sterol is cholesterol.
12. A method of treating a patient for a pulmonary infection comprising administering to the patient a therapeutically effective amount of the liposomal aminoglycoside formulation of claim 1.
13. The method of claim 12, wherein the pulmonary infection is a *Pseudomonas* staphylococcal, streptococcal, *Escherichia, Kiebsiella, Enterobacter, Serratia, Haemophilus, Yersinia, Burkholderia*, or *Mycobacterium* infection.
14. A method of treating a patient for a pulmonary infection in a cystic fibrosis patient comprising administering to the patient a therapeutically effective amount of the liposomal aminoglycoside formulation of claim 1.
15. The liposomal aminoglycoside formulation of claim 1, which is substantially free of anionic lipids.
16. The liposomal aminoglycoside formulation of claim 1, wherein the aminoglycoside is an aminoglycoside sulfate.
17. The liposomal aminoglycoside of claim 1, wherein the aminoglycoside is amikacin sulfate.
18. The liposomal aminoglycoside of claim 1, wherein the aminoglycoside is tobramycin sulfate.
19. The liposomal aminoglycoside of claim 1, wherein the aminoglycoside is gentamicin sulfate.
20. The method of claim 13, wherein the infection is a *Pseudomonas* infection.
21. The method of claim 20, wherein the *Pseudomonas* infection is selected from the group consisting of a *P. aeruginosa, P. paucimobilis, P. putida, P. fluorescens*, and *P. acidovorans* infection.
22. The method of claim 21, wherein the *Pseudomonas* infection is a *P. aeruginosa* infection.
23. The method of claim 13, wherein the infection is a staphylococcal infection.

24. The method of claim 23, wherein the staphylococcal infection is a Methicillin resistant *Staphylococcus aureus* (MRSA) infection.

25. The method of claim 13, wherein the infection is a streptococcal infection.

26. The method of claim 25, wherein the streptococcal infection is a *Streptococcus pneumoniae* infection.

27. The method of claim 13, wherein the infection is an *Escherichia* infection.

28. The method of claim 27, wherein the *Escherichia* infection is an *Escherichia coli* infection.

29. The method of claim 13, wherein the infection is a *Yersinia* infection.

30. The method of claim 29, wherein the *Yersinia* infection is a *Yersinia pesos* infection.

31. The method of claim 13, wherein the infection is a *Burkholderia* infection.

32. The method of claim 31, wherein the *Burkholderia* infection is selected from the group consisting of *Burkholderia pseudomallei, B. cepacia, B. gladioli, B. multivorans,* and *B. Vietnamiensis.*

33. The method of claim 13, wherein the infection is a *Mycobacterium* infection.

34. The method of claim 33, wherein the *Mycobacterium* infection is selected from the group consisting of *Mycobacterium tuberculosis, M avium complex* (MAC), *M avium, M intracellulare, M kansasii, M xenopi, M marinum, M ulcerans, M fortuitum complex, M fortuitum,* and *M chelonei.*

35. The liposomal aminoglycoside formulation of claim 2, wherein the aminoglycoside is selected from the group consisting of amikacin, gentamicin, and tobramycin.

36. The liposomal aminoglycoside formulation of claim 2, wherein the aminoglycoside is amikacin.

37. The liposomal aminoglycoside of claim 2, wherein the aminoglycoside is gentamicin.

38. The liposomal aminoglycoside of claim 2, wherein the aminoglycoside is tobramycin.

39. The liposomal aminoglycoside of claim 2, wherein the aminoglycoside is an aminoglycoside sulfate.

40. The liposomal aminoglycoside of claim 2, wherein the aminoglycoside is an amikacin sulfate.

41. The liposomal aminoglycoside of claim 2, wherein the aminoglycoside is tobramycin sulfate.

42. The liposomal aminoglycoside of claim 2, wherein the aminoglycoside is gentamicin sulfate.

43. The liposomal aminoglycoside of claim 2, wherein the neutral phospholipid is a phosphatidylcholine.

44. The liposomal aminoglycoside of claim 2, wherein the neutral phospholipid is DPPC.

45. The liposomal aminoglycoside of claim 2, wherein the sterol is cholesterol.

46. The liposomal aminoglycoside of claim 2, wherein the neutral phospholipid is DPPC and the sterol is cholesterol.

47. The liposomal aminoglycoside of claim 2, wherein the aminoglycoside is amikacin and the neutral phospholipid is DPPC.

48. The liposomal aminoglycoside of claim 2, wherein the aminoglycoside is amikacin and the sterol is cholesterol.

49. The liposomal aminoglycoside of claim 2, wherein the aminoglycoside is amikacin, the neutral phospholipid is DPPC and the sterol is cholesterol.

50. The liposomal aminoglycoside of claim 2, wherein the aminoglycoside is amikacin sulfate and the neutral phospholipid is DPPC.

51. The liposomal aminoglycoside of claim 2, wherein the aminoglycoside is amikacin sulfate and the sterol is cholesterol.

52. The liposomal aminoglycoside of claim 2, wherein the aminoglycoside is amikacin sulfate, the neutral phospholipid is DPPC and the sterol is cholesterol.

53. The liposomal aminoglycoside formulation of claim 3, wherein the aminoglycoside is selected from the group consisting of amikacin, gentamicin, and tobramycin.

54. The liposomal aminoglycoside formulation of claim 3, wherein the aminoglycoside is amikacin.

55. The liposomal aminoglycoside of claim 3, wherein the aminoglycoside is gentamicin.

56. The liposomal aminoglycoside of claim 3, wherein the aminoglycoside is tobramycin.

57. The liposomal aminoglycoside of claim 3, wherein the aminoglycoside is an aminoglycoside sulfate.

58. The liposomal aminoglycoside of claim 3, wherein the aminoglycoside is an amikacin sulfate.

59. The liposomal aminoglycoside of claim 3, wherein the aminoglycoside is tobramycin sulfate.

60. The liposomal aminoglycoside of claim 3, wherein the aminoglycoside is gentamicin sulfate.

61. The liposomal aminoglycoside of claim 3, wherein the neutral phospholipid is a phosphatidylcholine.

62. The liposomal aminoglycoside of claim 3, wherein the neutral phospholipid is DPPC.

63. The liposomal aminoglycoside of claim 3, wherein the sterol is cholesterol.

64. The liposomal aminoglycoside of claim 3, wherein the neutral phospholipid is DPPC and the sterol is cholesterol.

65. The liposomal aminoglycoside of claim 3, wherein the aminoglycoside is amikacin and the neutral phospholipid is DPPC.

66. The liposomal aminoglycoside of claim 3, wherein the aminoglycoside is amikacin and the sterol is cholesterol.

67. The liposomal aminoglycoside of claim 3, wherein the aminoglycoside is amikacin, the neutral phospholipid is DPPC and the sterol is cholesterol.

68. The liposomal aminoglycoside of claim 3, wherein the aminoglycoside is amikacin sulfate and the neutral phospholipid is DPPC.

69. The liposomal aminoglycoside of claim 3, wherein the aminoglycoside is amikacin sulfate and the sterol is cholesterol.

70. The liposomal aminoglycoside of claim 3, wherein the aminoglycoside is amikacin sulfate, the neutral phospholipid is DPPC and the sterol is cholesterol.

71. The liposomal aminoglycoside formulation of claim 1, wherein the amount of the lipid is less than or equal to 91% of the amount of the aminoglycoside by weight.

72. The liposomal aminoglycoside formulation of claim 1, wherein the amount of the lipid is less than or equal to 83% of the amount of the aminoglycoside by weight.

73. The liposomal aminoglycoside formulation of claim 1, wherein the amount of the lipid is less than or equal to 60% of the amount of the aminoglycoside by weight.

74. The liposomal aminoglycoside of claim 1, wherein the neutral phospholipid is a phosphatidylcholine.

75. The liposomal aminoglycoside of claim 1, wherein the aminoglycoside is amikacin and the neutral phospholipid is DPPC.

76. The liposomal aminoglycoside of claim 1, wherein the aminoglycoside is amikacin and the sterol is cholesterol.

77. The liposomal aminoglycoside of claim 1, wherein the aminoglycoside is amikacin sulfate and the neutral phospholinid is DPPC.

78. The liposomal aminoglycoside of claim 1, wherein the aminoglycoside is amikacin sulfate and the sterol is cholesterol.

79. The liposomal aminoglycoside of claim 1, wherein the aminoglycoside is amikacin sulfate, the neutral phospholipid is DPPC and the sterol is cholesterol.

\* \* \* \* \*

UNITED STATES PATENT AND TRADEMARK OFFICE
CERTIFICATE OF CORRECTION

PATENT NO. : 7,718,189 B2
APPLICATION NO. : 11/185448
DATED : May 18, 2010
INVENTOR(S) : Lawrence T. Boni et al.

It is certified that error appears in the above-identified patent and that said Letters Patent is hereby corrected as shown below:

IN THE CLAIMS

Column 38, line 40, in claim 13, replace "The method of claim 12, wherein the pulmonary infection is a Pseudomonas staphylococcal..." with --The method of claim 12, wherein the pulmonary infection is a Pseudomonas, staphylococcal...--.

Signed and Sealed this
Twenty-fourth Day of July, 2012

David J. Kappos
*Director of the United States Patent and Trademark Office*